(12) United States Patent
Kosmatopoulos et al.

(10) Patent No.: US 8,900,600 B2
(45) Date of Patent: Dec. 2, 2014

(54) IDENTIFICATION, OPTIMIZATION AND USE OF CRYPTIC HLA-A24 EPITOPES FOR IMMUNOTHERAPY

(75) Inventors: Kostantinos (Kostas) Kosmatopoulos, Paris (FR); Jeanne Menez-Jamet, Montrouge (FR)

(73) Assignee: VAXON Biotech, Paris (FR)

( * ) Notice: Subject to any disclaimer, the term of this patent is extended or adjusted under 35 U.S.C. 154(b) by 74 days.

(21) Appl. No.: 13/258,227

(22) PCT Filed: Apr. 2, 2009

(86) PCT No.: PCT/IB2009/005753
§ 371 (c)(1),
(2), (4) Date: Dec. 12, 2011

(87) PCT Pub. No.: WO2010/112962
PCT Pub. Date: Oct. 7, 2010

(65) Prior Publication Data
US 2012/0082692 A1 Apr. 5, 2012

(51) Int. Cl.
| | | |
|---|---|---|
| C07K 7/06 | (2006.01) | |
| C07K 4/12 | (2006.01) | |
| C07K 2/00 | (2006.01) | |
| A61K 38/03 | (2006.01) | |
| A61K 39/21 | (2006.01) | |
| C07K 14/005 | (2006.01) | |
| A61K 39/00 | (2006.01) | |
| A61K 38/00 | (2006.01) | |

(52) U.S. Cl.
CPC ..... *C07K 14/005* (2013.01); *C12N 2740/16322* (2013.01); *A61K 39/21* (2013.01); *C12N 2740/16222* (2013.01); *C07K 7/06* (2013.01); *A61K 39/00* (2013.01); *A61K 38/00* (2013.01); *C12N 2740/16034* (2013.01); *C12N 2740/16122* (2013.01); *Y10S 435/975* (2013.01)
USPC ............... 424/277.1; 530/328; 424/185.1; 424/192.1; 424/193.1; 514/19.3; 514/19.4; 514/19.5; 514/19.6; 514/21.6; 435/975

(58) Field of Classification Search
None
See application file for complete search history.

(56) References Cited

U.S. PATENT DOCUMENTS

2006/0018915 A1* 1/2006 Ishioka et al. ............. 424/184.1

FOREIGN PATENT DOCUMENTS

| EP | 1 462 456 | 9/2004 |
|---|---|---|
| EP | 1 715 042 | 10/2006 |
| WO | 99/50386 | 10/1999 |
| WO | WO 03/040165 A2 * | 5/2003 |
| WO | 2007/094924 | 8/2007 |
| WO | 2008/010010 | 1/2008 |

OTHER PUBLICATIONS

Ikuta et al. "A HER2/NEU-Derived Peptide, A Kd-Restricted Murine Tumor Rejection Antigen, Induces HER2-Specific HLA-A2402-Restricted CD81 Cytotoxic T Lymphocytes", Int. J. Cancer: 87, 553-558 (2000).*
Morishima, Identification of an HLA-A24-Restricted Cytotoxic T Lymphocyte Epitope from Human Papillomavirus Type-16 E6: The Combined Effects of Bortezomib and Interferon-Gamma on the Presentation of a Cryptic Epitope, International Journal of Cancer, 120, 594-604, 2006.
Ikuta et al., "A HER2/NEU-derived peptide, a K(d)-restricted murine tumor rejection antigen, induces HER2-specific HLA-A2402-restricted CD8(+) cytotoxic T lymphocytes," Int. J. Cancer, 87(4):553-8 (2007).
Nagata et al., "Peptides derived from a wild-type murine proto-oncogene c-erbB-2/HER2/neu can induce CTL and tumor suppression in syngeneic hosts," J. Immunol. 159(3):1336-43 (1997).

* cited by examiner

*Primary Examiner* — Ronald Schwadron
(74) *Attorney, Agent, or Firm* — Morgan, Lewis & Bockius LLP

(57) ABSTRACT

The present invention discloses peptides such as an isolated peptide consisting of an immunogenic HLA-A*2402-restricted epitope. For example, the isolated peptide may be selected from the group consisting of KYGVLLKTL (SEQ ID NO:11); RYMRQFVAL (SEQ ID NO: 12); RYVSRLLGI (SEQ ID NO: 13); RYGKGWDLL (SEQ ID NO: 14); RYLVQVQAL (SEQ ID NO: 15); and RYWELSNHL (SEQ ID NO: 16).

4 Claims, 2 Drawing Sheets

Figure 1:
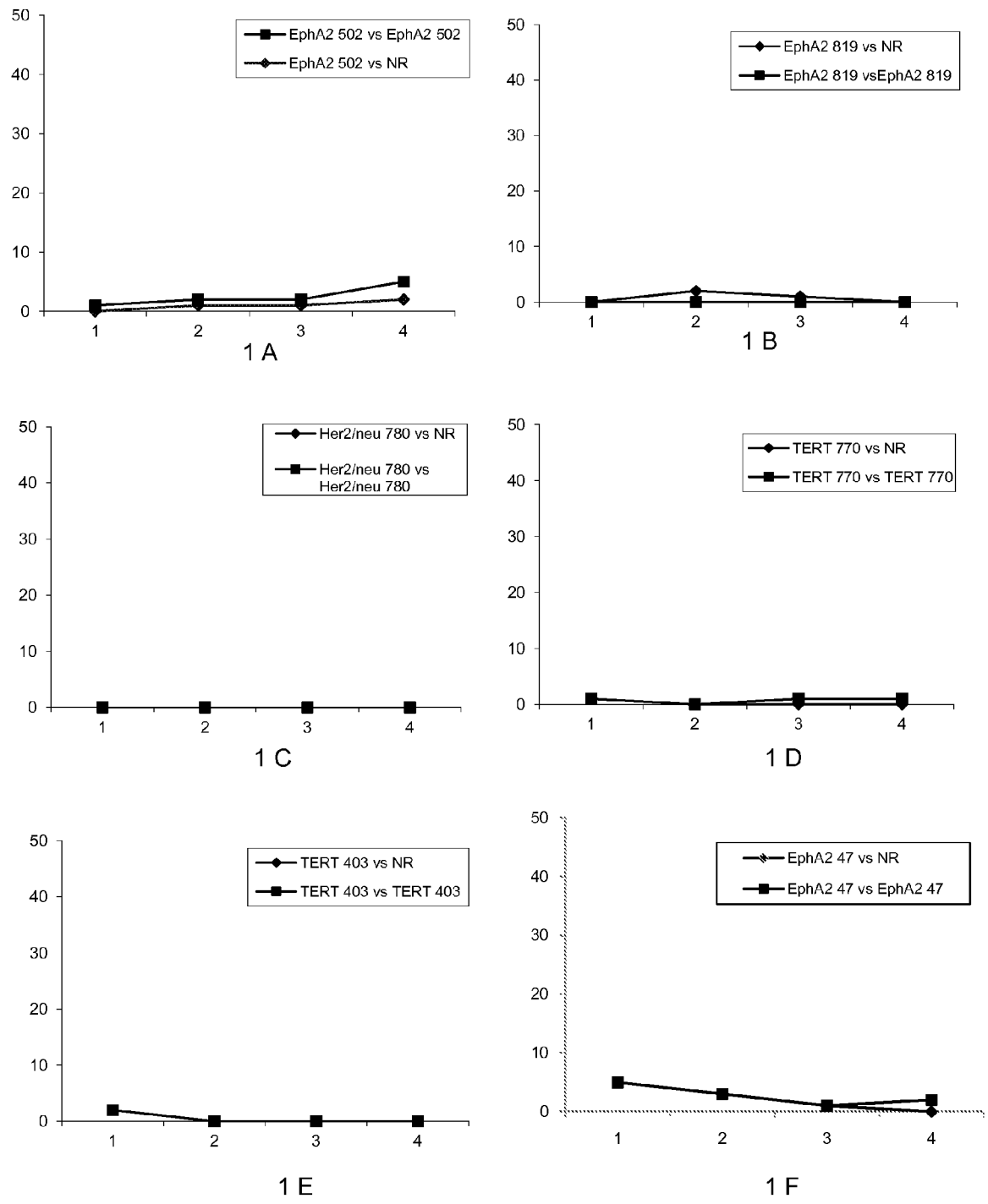

SEQUENCE LISTING

```
<160> NUMBER OF SEQ ID NOS: 190

<210> SEQ ID NO 1
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 1

Pro Tyr Gly Val Leu Leu Lys Thr His
1               5

<210> SEQ ID NO 2
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 2

Pro Tyr Met Arg Gln Phe Val Ala His
1               5

<210> SEQ ID NO 3
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 3

Pro Tyr Val Ser Arg Leu Leu Gly Ile
1               5

<210> SEQ ID NO 4
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 4

Pro Tyr Gly Lys Gly Trp Asp Leu Met
1               5

<210> SEQ ID NO 5
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 5
```

Thr Tyr Leu Val Gln Val Gln Ala Leu
1               5

<210> SEQ ID NO 6
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 6

Pro Tyr Trp Glu Leu Ser Asn His Glu
1               5

<210> SEQ ID NO 7
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 7

Pro Tyr Asp Gly Ile Pro Ala Arg Glu
1               5

<210> SEQ ID NO 8
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 8

Arg Tyr Glu Phe Leu Trp Gly Pro Arg
1               5

<210> SEQ ID NO 9
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 9

Pro Tyr Asn Tyr Leu Ser Thr Asp Val
1               5

<210> SEQ ID NO 10
<211> LENGTH: 9
<212> TYPE: PRT
<213> ORGANISM: Artificial
<220> FEATURE:
<223> OTHER INFORMATION: Cryptic HLA-A2402 restricted peptide

<400> SEQUENCE: 10

Pro Tyr Gly Cys Leu Leu Asp His Val
1               5

<210> SEQ ID NO 11
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 11

```
Lys Tyr Gly Val Leu Leu Lys Thr Leu
1               5

<210> SEQ ID NO 12
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 12

Arg Tyr Met Arg Gln Phe Val Ala Leu
1               5

<210> SEQ ID NO 13
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 13

Arg Tyr Val Ser Arg Leu Leu Gly Ile
1               5

<210> SEQ ID NO 14
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 14

Arg Tyr Gly Lys Gly Trp Asp Leu Leu
1               5

<210> SEQ ID NO 15
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 15

Arg Tyr Leu Val Gln Val Gln Ala Leu
1               5

<210> SEQ ID NO 16
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 16

Arg Tyr Trp Glu Leu Ser Asn His Leu
1               5

<210> SEQ ID NO 17
<211> LENGTH: 9
<212> TYPE: PRT
<213> ORGANISM: Artificial
<220> FEATURE:
```

```
<223> OTHER INFORMATION: Optimized peptide derived from cryptic peptides
      of SEQ ID Nos: 1 to 9

<400> SEQUENCE: 17

Arg Tyr Asp Gly Ile Pro Ala Arg Leu
1               5

<210> SEQ ID NO 18
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 18

Arg Tyr Glu Phe Leu Trp Gly Pro Leu
1               5

<210> SEQ ID NO 19
<211> LENGTH: 9
<212> TYPE: PRT
<213> ORGANISM: Artificial
<220> FEATURE:
<223> OTHER INFORMATION: Optimized peptide derived from cryptic peptides
      of SEQ ID Nos: 1 to 9

<400> SEQUENCE: 19

Arg Tyr Asn Tyr Leu Ser Thr Asp Leu
1               5

<210> SEQ ID NO 20
<211> LENGTH: 12
<212> TYPE: PRT
<213> ORGANISM: Artificial
<220> FEATURE:
<223> OTHER INFORMATION: Cryptic HLA-A2402 restricted peptide
<220> FEATURE:
<221> NAME/KEY: VARIANT
<222> LOCATION: (1)..(1)
<223> OTHER INFORMATION: Xaa can be any amino acid
<220> FEATURE:
<221> NAME/KEY: VARIANT
<222> LOCATION: (3)..(7)
<223> OTHER INFORMATION: Xaa can be any amino acid
<220> FEATURE:
<221> NAME/KEY: VARIANT
<222> LOCATION: (8)..(11)
<223> OTHER INFORMATION: Xaa can be any amino acid or none
<220> FEATURE:
<221> NAME/KEY: VARIANT
<222> LOCATION: (12)..(12)
<223> OTHER INFORMATION: Xaa can be any amino acid exept "Leu" or "Phe"
      or "Ile" if (1) = "Arg" or "Lys"

<400> SEQUENCE: 20

Xaa Tyr Xaa Xaa Xaa Xaa Xaa Xaa Xaa Xaa Xaa Xaa
1               5                   10

<210> SEQ ID NO 21
<211> LENGTH: 12
<212> TYPE: PRT
<213> ORGANISM: Artificial
<220> FEATURE:
<223> OTHER INFORMATION: Cryptic HLA-A2402 restricted peptide
<220> FEATURE:
<221> NAME/KEY: VARIANT
<222> LOCATION: (1)..(1)
<223> OTHER INFORMATION: Xaa can be any amino acid except "Arg" or "Lys"
<220> FEATURE:
<221> NAME/KEY: VARIANT
```

```
<222> LOCATION: (3)..(7)
<223> OTHER INFORMATION: Xaa can be any amino acid
<220> FEATURE:
<221> NAME/KEY: VARIANT
<222> LOCATION: (8)..(11)
<223> OTHER INFORMATION: Xaa can be any amino acid or none

<400> SEQUENCE: 21

Xaa Tyr Xaa Xaa Xaa Xaa Xaa Xaa Xaa Xaa Xaa Leu
1               5                   10

<210> SEQ ID NO 22
<211> LENGTH: 12
<212> TYPE: PRT
<213> ORGANISM: Artificial
<220> FEATURE:
<223> OTHER INFORMATION: Cryptic HLA-A2402 restricted peptide
<220> FEATURE:
<221> NAME/KEY: VARIANT
<222> LOCATION: (1)..(1)
<223> OTHER INFORMATION: Xaa can be any amino acid except "Arg" or "Lys"
<220> FEATURE:
<221> NAME/KEY: VARIANT
<222> LOCATION: (3)..(7)
<223> OTHER INFORMATION: Xaa can be any amino acid
<220> FEATURE:
<221> NAME/KEY: VARIANT
<222> LOCATION: (8)..(11)
<223> OTHER INFORMATION: Xaa can be any amino acid or none
<220> FEATURE:
<221> NAME/KEY: VARIANT
<222> LOCATION: (12)..(12)
<223> OTHER INFORMATION: Xaa can be any amino acid exept "Asp" or "Glu"
      or "Gly" or "His" or "Pro" or "Gln" or "Arg" or "Lys"

<400> SEQUENCE: 22

Xaa Tyr Xaa Xaa Xaa Xaa Xaa Xaa Xaa Xaa Xaa Xaa
1               5                   10

<210> SEQ ID NO 23
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 23

Ala Ala Gly Ile Gly Ile Leu Thr Val
1               5

<210> SEQ ID NO 24
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 24

Tyr Ala Gly Ile Gly Ile Leu Thr Val
1               5

<210> SEQ ID NO 25
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope
```

```
<400> SEQUENCE: 25

Glu Ala Ala Gly Ile Gly Ile Leu Thr Val
1               5                   10

<210> SEQ ID NO 26
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 26

Glu Leu Ala Gly Ile Gly Ile Leu Thr Val
1               5                   10

<210> SEQ ID NO 27
<211> LENGTH: 10
<212> TYPE: PRT
<213> ORGANISM: Artificial
<220> FEATURE:
<223> OTHER INFORMATION: paptide

<400> SEQUENCE: 27

Ala Met Leu Gly Thr His Thr Met Glu Val
1               5                   10

<210> SEQ ID NO 28
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 28

Tyr Met Leu Gly Thr His Thr Met Glu Val
1               5                   10

<210> SEQ ID NO 29
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 29

Met Leu Gly Thr His Thr Met Glu Val
1               5

<210> SEQ ID NO 30
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 30

Tyr Leu Gly Thr His Thr Met Glu Val
1               5

<210> SEQ ID NO 31
<211> LENGTH: 9
<212> TYPE: PRT
<213> ORGANISM: Artificial
```

```
<220> FEATURE:
<223> OTHER INFORMATION: Epitope which can be combined to HLA-A2402-
      restricted epitope

<400> SEQUENCE: 31

Lys Thr Trp Gly Gln Tyr Trp Gln Val
1               5

<210> SEQ ID NO 32
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 32

Tyr Thr Trp Gly Gln Tyr Trp Gln Val
1               5

<210> SEQ ID NO 33
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 33

Lys Met Trp Gly Gln Tyr Trp Gln Val
1               5

<210> SEQ ID NO 34
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 34

Ser Leu Ala Asp Thr Asn Ser Leu Ala Val
1               5                   10

<210> SEQ ID NO 35
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 35

Tyr Leu Ala Asp Thr Asn Ser Leu Ala Val
1               5                   10

<210> SEQ ID NO 36
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 36

Thr Asp Gln Val Pro Phe Ser Val
1               5
```

<210> SEQ ID NO 37
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 37

Tyr Asp Gln Val Pro Phe Ser Val
1               5

<210> SEQ ID NO 38
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 38

Tyr Met Gln Val Pro Phe Ser Val
1               5

<210> SEQ ID NO 39
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 39

Val Leu Tyr Arg Tyr Gly Ser Phe Ser Val
1               5                   10

<210> SEQ ID NO 40
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 40

Tyr Leu Tyr Arg Tyr Gly Ser Phe Ser Val
1               5                   10

<210> SEQ ID NO 41
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 41

Leu Leu Asp Gly Thr Ala Thr Leu Arg Leu
1               5                   10

<210> SEQ ID NO 42
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

```
<400> SEQUENCE: 42

Tyr Leu Asp Gly Thr Ala Thr Leu Arg Leu
1               5                   10

<210> SEQ ID NO 43
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 43

Gln Leu Met Pro Tyr Gly Cys Leu Leu
1               5

<210> SEQ ID NO 44
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 44

Tyr Leu Met Pro Tyr Gly Cys Leu Leu
1               5

<210> SEQ ID NO 45
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 45

Lys Ile Phe Gly Ser Leu Ala Phe Leu
1               5

<210> SEQ ID NO 46
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 46

Tyr Ile Phe Gly Ser Leu Ala Phe Leu
1               5

<210> SEQ ID NO 47
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 47

Cys Leu Thr Ser Thr Val Gln Leu Val
1               5

<210> SEQ ID NO 48
<211> LENGTH: 9
<212> TYPE: PRT
```

```
<213> ORGANISM: Artificial
<220> FEATURE:
<223> OTHER INFORMATION: Epitope which can be combined to HLA-A2402-
      restricted epitope

<400> SEQUENCE: 48

Tyr Leu Thr Ser Thr Val Gln Leu Val
1               5

<210> SEQ ID NO 49
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 49

His Leu Tyr Gln Gly Cys Gln Trp
1               5

<210> SEQ ID NO 50
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 50

Tyr Leu Tyr Gln Gly Cys Gln Trp
1               5

<210> SEQ ID NO 51
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 51

Val Met Ala Gly Val Gly Ser Pro Tyr Val
1               5                   10

<210> SEQ ID NO 52
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 52

Tyr Met Ala Gly Val Gly Ser Pro Tyr Val
1               5                   10

<210> SEQ ID NO 53
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 53

Ala Leu Cys Arg Trp Gly Leu Leu
1               5
```

<210> SEQ ID NO 54
<211> LENGTH: 8
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 54

Tyr Leu Cys Arg Trp Gly Leu Leu
1               5

<210> SEQ ID NO 55
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 55

Val Leu Val Lys Ser Pro Asn His Val
1               5

<210> SEQ ID NO 56
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 56

Tyr Leu Val Lys Ser Pro Asn His Val
1               5

<210> SEQ ID NO 57
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 57

Ile Leu Leu Val Val Val Leu Gly Val
1               5

<210> SEQ ID NO 58
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 58

Tyr Leu Leu Val Val Val Leu Gly Val
1               5

<210> SEQ ID NO 59
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

```
<400> SEQUENCE: 59

Pro Leu Thr Ser Ile Ile Ser Ala Val
1               5

<210> SEQ ID NO 60
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 60

Tyr Leu Thr Ser Ile Ile Ser Ala Val
1               5

<210> SEQ ID NO 61
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 61

Ala Leu Ile His His Asn Thr His Leu
1               5

<210> SEQ ID NO 62
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 62

Tyr Leu Ile His His Asn Thr His Leu
1               5

<210> SEQ ID NO 63
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 63

Thr Leu Glu Glu Ile Thr Gly Tyr Leu
1               5

<210> SEQ ID NO 64
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 64

Tyr Leu Glu Glu Ile Thr Gly Tyr Leu
1               5

<210> SEQ ID NO 65
<211> LENGTH: 9
```

-continued

```
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 65

Pro Leu Gln Pro Glu Gln Leu Gln Val
1               5

<210> SEQ ID NO 66
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 66

Tyr Leu Gln Pro Glu Gln Leu Gln Val
1               5

<210> SEQ ID NO 67
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 67

Glu Leu Val Ser Glu Phe Ser Arg Met
1               5

<210> SEQ ID NO 68
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 68

Tyr Leu Val Ser Glu Phe Ser Arg Met
1               5

<210> SEQ ID NO 69
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 69

Asp Met Pro Ile Tyr Met Tyr Ser Val
1               5

<210> SEQ ID NO 70
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 70

Tyr Met Pro Ile Tyr Met Tyr Ser Val
```

<210> SEQ ID NO 71
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 71

Thr Val Trp Glu Leu Met Thr Phe Gly Ala
1               5                   10

<210> SEQ ID NO 72
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 72

Thr Ile Trp Glu Leu Met Thr Phe Gly Gly
1               5                   10

<210> SEQ ID NO 73
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 73

Thr Val Trp Glu Leu Met Thr Phe Gly Ser
1               5                   10

<210> SEQ ID NO 74
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 74

Tyr Val Trp Glu Leu Met Thr Phe Gly Val
1               5                   10

<210> SEQ ID NO 75
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 75

Lys Val Lys Val Leu Gly Ser Gly Ala
1               5

<210> SEQ ID NO 76
<211> LENGTH: 9
<212> TYPE: PRT
<213> ORGANISM: Artificial
<220> FEATURE:
<223> OTHER INFORMATION: Epitope which can be combined to HLA-A2402-

-continued

<400> SEQUENCE: 76

Lys Leu Lys Val Leu Gly Ser Gly Val
1               5

<210> SEQ ID NO 77
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 77

Arg Val Lys Val Leu Gly Ser Gly Ala
1               5

<210> SEQ ID NO 78
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 78

Lys Ile Lys Val Leu Gly Ser Gly Ala
1               5

<210> SEQ ID NO 79
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 79

Tyr Val Lys Val Leu Gly Ser Gly Val
1               5

<210> SEQ ID NO 80
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 80

Asp Leu Ala Ala Arg Asn Val Leu Val
1               5

<210> SEQ ID NO 81
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 81

Asn Leu Ala Ala Arg Asn Val Leu Leu
1               5

<210> SEQ ID NO 82

-continued

```
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 82

Tyr Leu Ala Ala Arg Asn Val Leu Val
1               5

<210> SEQ ID NO 83
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 83

Asp Val Trp Ser Tyr Gly Val Thr Val
1               5

<210> SEQ ID NO 84
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 84

Asp Val Trp Ser Tyr Gly Val Thr Ile
1               5

<210> SEQ ID NO 85
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 85

Tyr Val Trp Ser Tyr Gly Val Thr Val
1               5

<210> SEQ ID NO 86
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 86

Asp Leu Leu Glu Lys Gly Glu Arg Leu
1               5

<210> SEQ ID NO 87
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 87
```

```
Ser Ile Leu Glu Leu Lys Gly Glu Arg Leu
1               5                   10

<210> SEQ ID NO 88
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 88

Tyr Leu Leu Glu Lys Gly Glu Arg Leu
1               5

<210> SEQ ID NO 89
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 89

Pro Ile Cys Thr Ile Asp Val Tyr Met Ile
1               5                   10

<210> SEQ ID NO 90
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 90

Gln Ile Cys Thr Ile Asp Val Tyr Met Val
1               5                   10

<210> SEQ ID NO 91
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 91

Pro Ile Cys Thr Ile Asp Val Tyr Met Val
1               5                   10

<210> SEQ ID NO 92
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 92

Pro Ile Cys Thr Ile Asp Val Tyr Lys Ile
1               5                   10

<210> SEQ ID NO 93
<211> LENGTH: 10
<212> TYPE: PRT
<213> ORGANISM: Artificial
<220> FEATURE:
```

```
<223> OTHER INFORMATION: Epitope which can be combined to HLA-A2402-
      restricted epitope

<400> SEQUENCE: 93

Tyr Ile Cys Thr Ile Asp Val Tyr Met Val
1               5                   10

<210> SEQ ID NO 94
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 94

Tyr Leu Glu Tyr Arg Gln Val Pro Gly
1               5

<210> SEQ ID NO 95
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 95

Tyr Leu Glu Tyr Arg Gln Val Pro Asp
1               5

<210> SEQ ID NO 96
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 96

Tyr Leu Glu Tyr Arg Gln Val Pro Val
1               5

<210> SEQ ID NO 97
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 97

Asp Leu Gln Val Asn Ser Leu Gln Thr Val
1               5                   10

<210> SEQ ID NO 98
<211> LENGTH: 10
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 98

Tyr Leu Gln Val Asn Ser Leu Gln Thr Val
1               5                   10
```

```
<210> SEQ ID NO 99
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 99

Arg Leu Phe Phe Tyr Arg Lys Ser Val
1               5

<210> SEQ ID NO 100
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 100

Tyr Leu Phe Phe Tyr Arg Lys Ser Val
1               5

<210> SEQ ID NO 101
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 101

Asp Pro Arg Arg Leu Val Gln Leu Leu
1               5

<210> SEQ ID NO 102
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 102

Ala Pro Arg Arg Leu Val Gln Leu Leu
1               5

<210> SEQ ID NO 103
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 103

Ser Pro Arg Leu Gln Leu Ser Asn Gly
1               5

<210> SEQ ID NO 104
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 104
```

```
Ser Pro Arg Leu Gln Leu Ser Asn Leu
1               5

<210> SEQ ID NO 105
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 105

Ala Pro Arg Ser Pro Leu Ala Pro Ser
1               5

<210> SEQ ID NO 106
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 106

Ala Pro Arg Ser Pro Leu Ala Pro Leu
1               5

<210> SEQ ID NO 107
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 107

Ser Pro Lys Ala Asn Lys Glu Ile Leu
1               5

<210> SEQ ID NO 108
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 108

Ala Pro Lys Ala Asn Lys Glu Ile Leu
1               5

<210> SEQ ID NO 109
<211> LENGTH: 9
<212> TYPE: PRT
<213> ORGANISM: Artificial
<220> FEATURE:
<223> OTHER INFORMATION: Epitope which can be combined to HLA-A2402-
      restricted epitope

<400> SEQUENCE: 109

Gly Pro Lys His Ser Asp Cys Leu Ala
1               5

<210> SEQ ID NO 110
<211> LENGTH: 9
<212> TYPE: PRT
<213> ORGANISM: Artificial
```

```
<220> FEATURE:
<223> OTHER INFORMATION: Epitope which can be combined to HLA-A2402-
      restricted epitope

<400> SEQUENCE: 110

Ala Pro Lys His Ser Asp Cys Leu Ala
1               5

<210> SEQ ID NO 111
<211> LENGTH: 9
<212> TYPE: PRT
<213> ORGANISM: Artificial
<220> FEATURE:
<223> OTHER INFORMATION: Reference peptide standard A24

<400> SEQUENCE: 111

Ala Tyr Ile Asp Asn Tyr Asn Lys Phe
1               5

<210> SEQ ID NO 112
<211> LENGTH: 13
<212> TYPE: PRT
<213> ORGANISM: Artificial
<220> FEATURE:
<223> OTHER INFORMATION: I-Ab restricted HBVcore128 T helper epitope

<400> SEQUENCE: 112

Thr Pro Pro Ala Tyr Arg Pro Pro Asn Ala Pro Ile Leu
1               5                   10

<210> SEQ ID NO 113
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 113

Ser Tyr Leu Asp Ser Gly Ile His Phe
1               5

<210> SEQ ID NO 114
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 114

Asn Tyr Asn Asn Phe Tyr Arg Phe Leu
1               5

<210> SEQ ID NO 115
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 115

Glu Tyr Ser Lys Glu Cys Leu Lys Glu Phe
1               5                   10

<210> SEQ ID NO 116
```

```
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 116

Glu Tyr Leu Ser Leu Ser Asp Lys Ile
1               5

<210> SEQ ID NO 117
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 117

Glu Tyr Leu Gln Leu Val Phe Gly Ile
1               5

<210> SEQ ID NO 118
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 118

Thr Phe Pro Asp Leu Glu Ser Glu Phe
1               5

<210> SEQ ID NO 119
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 119

Val Ala Glu Leu Val His Phe Leu Leu
1               5

<210> SEQ ID NO 120
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 120

Asn Tyr Lys Arg Cys Phe Pro Val Ile
1               5

<210> SEQ ID NO 121
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 121
```

```
Leu Tyr Ala Thr Val Ile His Asp Ile
1               5
```

<210> SEQ ID NO 122
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 122

```
Gln Tyr Ser Trp Phe Val Asn Gly Thr Phe
1               5                   10
```

<210> SEQ ID NO 123
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 123

```
Thr Tyr Ala Cys Phe Val Ser Asn Leu
1               5
```

<210> SEQ ID NO 124
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 124

```
Val Tyr Phe Phe Leu Pro Asp His Leu
1               5
```

<210> SEQ ID NO 125
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 125

```
Leu Tyr Ser Ala Cys Phe Trp Trp Leu
1               5
```

<210> SEQ ID NO 126
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 126

```
Ala Phe Leu Pro Trp His Arg Leu Phe
1               5
```

<210> SEQ ID NO 127
<211> LENGTH: 9
<212> TYPE: PRT
<213> ORGANISM: Artificial
<220> FEATURE:

```
<223> OTHER INFORMATION: Tumor and HIV derived HLA-A2402 restricted
      epitope

<400> SEQUENCE: 127

Arg Tyr Gln Leu Asp Pro Lys Phe Ile
1               5

<210> SEQ ID NO 128
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 128

Thr Tyr Leu Pro Thr Asn Ala Ser Leu
1               5

<210> SEQ ID NO 129
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 129

Leu Tyr Val Asp Ser Leu Phe Phe Leu
1               5

<210> SEQ ID NO 130
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 130

Asn Tyr Ala Arg Thr Glu Asp Phe Phe
1               5

<210> SEQ ID NO 131
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 131

Asn Ser Gln Pro Val Trp Leu Cys Leu
1               5

<210> SEQ ID NO 132
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 132

Thr Tyr Val Pro Leu Leu Gly Ser Leu
1               5
```

```
<210> SEQ ID NO 133
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 133

Cys Tyr Gly Asp Met Glu Asn Lys Leu
1               5

<210> SEQ ID NO 134
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 134

Ala Val Gln Val Cys Gly Pro Pro Leu
1               5

<210> SEQ ID NO 135
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 135

Cys Met Thr Trp Asn Gln Met Asn Leu
1               5

<210> SEQ ID NO 136
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 136

His Tyr Met Leu Lys His Leu Val Trp
1               5

<210> SEQ ID NO 137
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 137

Lys Tyr Lys Leu Lys His Ile Val Trp
1               5

<210> SEQ ID NO 138
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 138
```

```
Leu Tyr Asn Thr Val Ala Thr Leu
1               5

<210> SEQ ID NO 139
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 139

Leu Tyr Cys Val His Gln Lys Ile
1               5

<210> SEQ ID NO 140
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 140

Asn Tyr Pro Ile Val Gln Asn Leu
1               5

<210> SEQ ID NO 141
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 141

Glu Ile Tyr Lys Arg Trp Ile Ile Leu
1               5

<210> SEQ ID NO 142
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 142

Ile Tyr Lys Arg Trp Ile Ile Leu
1               5

<210> SEQ ID NO 143
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 143

Ile Tyr Lys Arg Trp Ile Ile Leu Gly Leu
1               5                   10

<210> SEQ ID NO 144
<211> LENGTH: 10
<212> TYPE: PRT
<213> ORGANISM: Artificial
```

```
<220> FEATURE:
<223> OTHER INFORMATION: Tumor and HIV derived HLA-A2402 restricted
      epitope

<400> SEQUENCE: 144

Leu Tyr Pro Leu Ala Ser Leu Arg Ser Leu
1               5                   10

<210> SEQ ID NO 145
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 145

Asp Ala Tyr Phe Ser Val Pro Leu
1               5

<210> SEQ ID NO 146
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 146

Val Tyr Tyr Asp Pro Ser Lys Asp Leu
1               5

<210> SEQ ID NO 147
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 147

Ile Tyr Gln Glu Pro Phe Lys Asn Leu
1               5

<210> SEQ ID NO 148
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 148

Gly Tyr Ile Glu Ala Glu Val Ile
1               5

<210> SEQ ID NO 149
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 149

Leu Phe Cys Ala Ser Asp Ala Lys Ala Tyr
1               5                   10
```

```
<210> SEQ ID NO 150
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 150

Arg Tyr Leu Arg Asp Gln Gln Leu
1               5

<210> SEQ ID NO 151
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 151

Arg Tyr Leu Lys Asp Gln Gln Leu Leu
1               5

<210> SEQ ID NO 152
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 152

Arg Tyr Leu Arg Asp Gln Gln Leu Leu
1               5

<210> SEQ ID NO 153
<211> LENGTH: 11
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 153

Arg Tyr Leu Arg Asp Gln Gln Leu Leu Gly Ile
1               5                   10

<210> SEQ ID NO 154
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 154

Tyr Leu Lys Asp Gln Gln Leu Leu
1               5

<210> SEQ ID NO 155
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope
```

```
<400> SEQUENCE: 155

Tyr Leu Arg Asp Gln Gln Leu Leu
1               5

<210> SEQ ID NO 156
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 156

Trp Tyr Ile Lys Ile Phe Ile Met Ile
1               5

<210> SEQ ID NO 157
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 157

Ser Tyr Arg Arg Leu Arg Asp Leu Leu
1               5

<210> SEQ ID NO 158
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 158

Thr Tyr Lys Ala Ala Val Asp Leu
1               5

<210> SEQ ID NO 159
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 159

His Ser Gln Arg Arg Gln Asp Ile Leu
1               5

<210> SEQ ID NO 160
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 160

Arg Gln Asp Ile Leu Asp Leu Trp Ile
1               5

<210> SEQ ID NO 161
<211> LENGTH: 9
<212> TYPE: PRT
```

<213> ORGANISM: Artificial
<220> FEATURE:
<223> OTHER INFORMATION: Tumor and HIV derived HLA-A2402 restricted
      epitope

<400> SEQUENCE: 161

Gly Tyr Phe Pro Asp Trp Gln Asn Tyr
1               5

<210> SEQ ID NO 162
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 162

Asn Tyr Thr Pro Gly Pro Gly Val Arg Tyr
1               5                   10

<210> SEQ ID NO 163
<211> LENGTH: 8
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 163

Arg Tyr Pro Leu Thr Phe Gly Trp
1               5

<210> SEQ ID NO 164
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 164

Arg Tyr Pro Leu Thr Phe Gly Trp Cys Phe
1               5                   10

<210> SEQ ID NO 165
<211> LENGTH: 10
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 165

Arg Tyr Pro Leu Thr Phe Gly Trp Cys Tyr
1               5                   10

<210> SEQ ID NO 166
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 166

Asp Ser Arg Leu Ala Phe His His Met
1               5

<210> SEQ ID NO 167
<211> LENGTH: 9
<212> TYPE: PRT
<213> ORGANISM: Artificial
<220> FEATURE:
<223> OTHER INFORMATION: Tumor and HIV derived HLA-A2402 restricted
      epitope

<400> SEQUENCE: 167

Ala Phe His His Val Ala Arg Glu Leu
1               5

<210> SEQ ID NO 168
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 168

Ser Tyr Leu Asp Ser Gly Ile His Phe
1               5

<210> SEQ ID NO 169
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 169

Thr Tyr Val Pro Leu Leu Gly Ser Leu
1               5

<210> SEQ ID NO 170
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 170

Cys Tyr Gly Asp Met Glu Asn Lys Leu
1               5

<210> SEQ ID NO 171
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 171

Ala Val Gln Val Cys Gly Pro Pro Leu
1               5

<210> SEQ ID NO 172
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 172

Asn Tyr Asn Asn Phe Tyr Arg Phe Leu
1               5

<210> SEQ ID NO 173
<211> LENGTH: 10
<212> TYPE: PRT
<213> ORGANISM: Artificial
<220> FEATURE:
<223> OTHER INFORMATION: Tumor immunogenic HLA- A24 T cell epitope

<400> SEQUENCE: 173

Glu Tyr Ser Lys Glu Cys Leu Lys Glu Phe
1               5                   10

<210> SEQ ID NO 174
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 174

Glu Tyr Leu Ser Leu Ser Asp Lys Ile
1               5

<210> SEQ ID NO 175
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 175

Glu Tyr Leu Gln Leu Val Phe Gly Ile
1               5

<210> SEQ ID NO 176
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 176

Thr Phe Pro Asp Leu Glu Ser Glu Phe
1               5

<210> SEQ ID NO 177
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 177

Val Ala Glu Leu Val His Phe Leu Leu
1               5

<210> SEQ ID NO 178
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 178

Asn Tyr Lys Arg Cys Phe Pro Val Ile
1               5

<210> SEQ ID NO 179
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 179

Leu Tyr Ala Thr Val Ile His Asp Ile
1               5

<210> SEQ ID NO 180
<211> LENGTH: 10
<212> TYPE: PRT
<213> ORGANISM: Artificial
<220> FEATURE:
<223> OTHER INFORMATION: Tumor immunogenic HLA- A24 T cell epitope

<400> SEQUENCE: 180

Gln Tyr Ser Trp Phe Val Asn Gly Thr Phe
1               5                   10

<210> SEQ ID NO 181
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 181

Thr Tyr Ala Cys Phe Val Ser Asn Leu
1               5

<210> SEQ ID NO 182
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 182

Val Tyr Phe Phe Leu Pro Asp His Leu
1               5

<210> SEQ ID NO 183
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 183

Leu Tyr Ser Ala Cys Phe Trp Trp Leu
1               5

<210> SEQ ID NO 184
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 184

Ala Phe Leu Pro Trp His Arg Leu Phe
1               5

```
<210> SEQ ID NO 185
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 185

Arg Tyr Gln Leu Asp Pro Lys Phe Ile
1               5

<210> SEQ ID NO 186
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 186

Thr Tyr Leu Pro Thr Asn Ala Ser Leu
1               5

<210> SEQ ID NO 187
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 187

Leu Tyr Val Asp Ser Leu Phe Phe Leu
1               5

<210> SEQ ID NO 188
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 188

Asn Tyr Ala Arg Thr Glu Asp Phe Phe
1               5

<210> SEQ ID NO 189
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 189

Asn Ser Gln Pro Val Trp Leu Cys Leu
1               5

<210> SEQ ID NO 190
<211> LENGTH: 9
<212> TYPE: PRT
<213> ORGANISM: Artificial
<220> FEATURE:
<223> OTHER INFORMATION: Tumor immunogenic HLA- A24 T cell epitope

<400> SEQUENCE: 190

Cys Met Thr Trp Asn Gln Met Asn Leu
1               5
```

IDENTIFICATION, OPTIMIZATION AND USE OF CRYPTIC HLA-A24 EPITOPES FOR IMMUNOTHERAPY

RELATED APPLICATIONS

The present application is a U.S. National Phase Application of International Application No. PCT/IB2009/005753 (filed Apr. 2, 2009) which is hereby incorporated by reference in its entirety.

SEQUENCE LISTING SUBMISSION VIA EFS-WEB

A computer readable text file, entitled "045636-5175_SequenceListing.txt," created on or about Dec. 12, 2011, with a file size of about 43 kb contains the sequence listing for this application and is hereby incorporated by reference in its entirety.

The present invention relates to the field of peptide immunotherapy. In particular, the invention provides novel methods and materials for efficiently treating patients having an HLA-A*2402 phenotype.

Peptide vaccination or immunotherapy is a therapeutic approach which is currently the subject of a great number of studies in the context of the treatment of cancer. The principle thereof is based on immunization with peptides which reproduce T cell epitopes of tumor antigens recognized by cytotoxic T lymphocytes (CTLs), which play a major role in the elimination of tumor cells.

It will be recalled that CTLs do not recognize whole protein antigens, but peptide fragments thereof, generally comprising 8 to 10 amino acids, presented by class I major histocompatibility complex (MHC I) molecules expressed on the surface of cells. The presentation of these peptides is the result of the antigen processing which involves three steps:

cytosolic degradation of the antigen by a multienzyme complex called proteasome,
 translocation of the peptides derived from this degradation in the endoplasmic reticulum (ER) by the TAP transporters,
 association of these peptides with the MHC I molecules and exportation of the peptide/MHC I complexes to the cell surface.

The peptide/MHC I complexes interact with the specific T cell receptor (TCR) on CTL, inducing the stimulation and amplification of these CTL, which become able to attack target cells expressing the antigen from which the peptide is derived.

During the antigen processing, a peptide selection takes place, which results in a hierarchy of peptides presentation. Peptides that are preferentially presented by the MHC I molecules are called immunodominant, while peptides which are weakly presented are called cryptic. Immunodominant peptides exhibit a high affinity for the MHC I and are immunogenic while cryptic peptides exhibit a low affinity for MHC I and are non-immunogenic.

Immunodominant peptides have been widely targeted by tumor vaccines in preclinical and clinical studies with disappointing results (Gross et al., 2004; Rosenberg et al., 2004).

Tumor antigens are frequently self proteins over-expressed by tumors and expressed at lower levels by normal cells and tissues. The immune system is unable to react against these self antigens because of the self tolerance process. Self-tolerance concerns mainly the immunodominant peptides (Cibotti et al., 1992; Gross et al., 2004), thus explaining the incapacity of these peptides to induce a tumor immunity.

Cryptic peptides are much less involved in self tolerance process (Cibotti et al., 1992; Gross et al., 2004; Moudgil et al., 1999) and can therefore induce an efficient tumor immunity, provided their immunogenicity is enhanced (Engelhorn et al., 2006; Gross et al., 2004).

The usual strategy for enhancing the immunogenicity of cryptic peptides, which are non-immunogenic because of their low MHC I affinity, consists in increasing their affinity for the MHC I molecules via amino acids substitutions. Peptide affinity for MHC I molecules mainly depends on the presence at well defined positions (primary anchor positions) of residues called "primary anchor residues". These residues are MHC I allele specific. The presence of primary anchor residues, although often necessary, is not sufficient to ensure a high MHC I affinity. It has been shown that residues located outside the primary anchor positions (secondary anchor residues) may exert a favourable or unfavourable effect on the affinity of the peptide for the MHC I. The presence of these secondary anchor residues makes it possible to explain the existence, within peptides having the primary anchor motifs, of a great variability in the binding affinity (Ruppert et al., 1993).

Amino acids substitutions aiming at enhancing affinity for MHC I molecule should preserve the antigenicity of such optimized peptides. Indeed, CTL generated by optimized peptides must cross-react with the corresponding native peptides.

Many teams have succeeded in enhancing immunogenicity of already immunogenic peptides by increasing their affinity for HLA-A*0201 (Bakker et al., 1997; Parkhurst et al., 1996; Valmori et al., 1998). The inventors have previously described a general strategy to enhance affinity and immunogenicity of HLA-A*0201 restricted cryptic peptides (Scardino et al., 2002; Tourdot and Gould, 2002) and HLA-B*0702 (WO 2008/010098).

HLA-A*2402 is a frequently expressed molecule (27% of the population) and is one of the most common alleles in Japanese and Asian people. Identification and optimization of HLA-A*2402 restricted tumor cryptic peptides is therefore necessary for developing efficient cancer vaccines for HLA-A*2402 expressing patients.

Several tumor immunogenic peptides presented by HLA-A*2402 have been described to date (table 1).

TABLE 1

Tumor immunogenic HLA-A24 T cell epitopes

| Antigen | Sequence | SEQ ID No: |
|---|---|---|
| Beta-catenin | SYLDSGIHF | 168 |
| TERT | TYVPLLGSL | 169 |
| TERT | CYGDMENKL | 170 |
| TERT | AVQVCGPPL | 171 |
| KM-HN-1 | NYNNFYRFL | 172 |
| KM-HN-1 | EYSKECLKEF | 173 |
| KM-HN-1 | EYLSLSDKI | 174 |
| MAGE-A2 | EYLQLVFGI | 175 |
| MAGE-A3 | TFPDLESEF | 176 |
| MAGE-A3 | VAELVHFLL | 177 |
| MAGE-A4 | NYKRCFPVI | 178 |

TABLE 1-continued

Tumor immunogenic HLA-A24 T cell epitopes

| Antigen | Sequence | SEQ ID No: |
|---|---|---|
| SAGE | LYATVIHDI | 179 |
| CEA | QYSWFVNGTF | 180 |
| CEA | TYACFVSNL | 181 |
| gp100/Pmel17 | VYFFLPDHL | 182 |
| OA1 | LYSACFWWL | 183 |
| tyrosinase | AFLPWHRLF | 184 |
| Ep-CAM | RYQLDPKFI | 185 |
| Her2/neu | TYLPTNASL | 186 |
| PRAME | LYVDSLFFL | 187 |
| PSMA | NYARTEDFF | 188 |
| RNF43 | NSQPVWLCL | 189 |
| WT1 | CMTWNQMNL | 190 |

As described in the experimental part below, the inventors have now found a strategy to identify, in an antigen, cryptic peptides presented by HLA-A*2402 molecule, and to optimize their immunogenicity, preserving the cross-reactivity with the corresponding native cryptic peptides.

Hence, a first aspect of the present invention is a method for identifying an HLA-A*2402-restricted cryptic epitope in an antigen, comprising a step of selecting, in said antigen, a peptide of 8 to 12 amino acids having a tyrosine (Y) in primary anchor position 2, with the proviso that the peptide does not have, simultaneously, a positively charged amino acid (arginine (R) or lysine (K)) in position 1 and a leucine (L), or a phenylalanine (F) or an isoleucine (I) in C-terminal position. Such an epitope hence has the sequence $X_1YX_2X_3X_4X_5X_6X_7X_8X_9X_{10}X_{11}$ (SEQ ID No: 20), wherein $X_1$ to $X_6$ are any amino acid, $X_7$ to $X_{10}$ are any amino acid or none, and $X_{11} \neq L$ or F or I if $X_1 = R$ or K.

When the above selection step is performed alone, the obtained sequences are those of putative cryptic epitopes. Although epitopes responding to the above criteria have a strong probability to be non immunogenic, functional tests are necessary to identify truly cryptic epitopes with certainty. In particular, the inventors have observed that some peptides having a primary sequence as defined above are in fact immunogenic in individuals expressing HLA-A*2402. Hence, in a preferred embodiment, the method for identifying a HLA-A*2402-restricted cryptic epitope in an antigen further comprises step consisting in testing the immunogenicity of each putative cryptic epitope of SEQ ID No: 20, in an appropriate model, and selecting those which are non-immunogenic.

For performing this aspect of the invention, an appropriate model is a model which predicts the immunogenicity of the peptide in an individual who expresses HLA-A*2402. An example of such an appropriate model is described in the experimental part and consists of HLA-A*2402 transgenic mice. In this model, the non-immunogenicity of putative cryptic peptides is checked by vaccinating the mice and testing if specific CTL have been generated, by using human cells expressing HLA-A*2402 and loaded with the peptide as target cells.

In what follows, the phrases "HLA-A*2402-restricted cryptic epitope" or "native peptide" will be used to designate any peptide of SEQ ID No: 20, whether its non-immunogenicity has been checked or not. When necessary, the phrase "putative HLA-A*2402-restricted cryptic epitope" will be used to express the fact that the immunogenicity of the peptide has not been tested, and the phrase "confirmed HLA-A*2402-restricted cryptic epitope" will be used for peptides which have been tested and have proved to be non-immunogenic in an appropriate model.

In the present text, the term "peptide" designates not only molecules in which amino acid residues (in L or D configurations) are joined by peptide (—CO—NH—) linkages, but also synthetic pseudopeptides or peptidomimetics in which the peptide bond is modified, especially to become more resistant to proteolysis, and provided their immunogenicity is not impaired by this modification.

According to a preferred embodiment of the invention, the selected peptide has 9 to 11 amino acids, more preferably 9 or 10 amino acids and one or more unfavourable amino acids at secondary anchor positions, for example a P (proline) in position 1 and/or a D or E or G or H or P or Q or R or K (glutamic or aspartic acid, glycine, histidine, proline, glutamine, arginine or lysine) at C-terminal position.

A second aspect of the present invention is a method for increasing the immunogenicity of a HLA-A*2402-restricted cryptic epitope, comprising a step of substituting the N-terminal residue of said epitope with a positively charged amino acid (R or K), and/or substituting the C-terminal residue of said epitope with an L, F or I. Preferentially, the C-terminal modification is the substitution by an L.

Of course, in this method, the word "substituting" is to be understood as obtaining a peptide the sequence of which is derived from the sequence of said HLA-A*2402-restricted cryptic epitope by the mentioned substitution, whatever the technical method used to obtain said peptide. For example, the peptide can be produced by artificial peptide synthesis or by recombinant expression.

In particular, the immunogenicity of a HLA-A*2402-restricted cryptic epitope in which the two first residues are RY or KY can be increased by replacing its last amino-acid by an L, F or I, preferentially by an L (or by adding a L, I or F at its C-terminus, provided it is not longer than 11 amino acids). When the sequence of the selected HLA-A*2402-restricted cryptic epitope is $X_1YX_2X_3X_4X_5X_6X_7X_8X_9X_{10}L$ (SEQ ID No: 21), wherein $X_1$ is any amino acid but R or K, $X_2$ to $X_6$ are any amino acid, and $X_7$ to $X_{10}$ are any amino acid or none, the substitution of $X_1$ by R or K is sufficient to increase its immunogenicity. More generally, when the sequence of the selected HLA-A*2402-restricted cryptic epitope is $X_1YX_2X_3X_4X_5X_6X_7X_8X_9X_{10}X_{11}$ (SEQ ID No: 22), wherein $X_1$ is any amino acid but R or K, $X_2$ to $X_6$ are any amino acid, and $X_7$ to $X_{10}$ are any amino acid or none, and $X_{11}$ is not an unfavourable amino acids (D or E or G or H or P or Q or R or K), the substitution of $X_1$ by R or K can be sufficient to increase its immunogenicity.

In what follows, the expression "optimized peptide" or "optimized immunogenic A*2402-restricted epitope" will designate an immunogenic peptide derived from a HLA-A*2402-restricted cryptic epitope (called its "cognate native peptide") by the above method.

In a preferred embodiment of the invention, the optimized peptide can trigger an immune response which cross-recognizes its cognate native peptide. Another aspect of the present invention is hence a method for obtaining a HLA-A*2402- restricted epitope able to trigger an immune response against a HLA-A*2402-restricted cryptic epitope of an antigen, comprising the steps of (i) identifying, in said antigen, one or several native putative HLA-A*2402-restricted cryptic epitopes, by the method according to claim 1;

(ii) testing the immunogenicity of each native epitope selected in step (i), in an appropriate model, and selecting those which are non-immunogenic;

(iii) for each native epitope selected in step (ii), obtaining an optimized epitope by increasing its immunogenicity, by the method as above-described;

(iv) testing the immunogenicity of each optimized epitope obtained in step (iii), in an appropriate model, and selecting those which are immunogenic;

(v) for each epitope selected in step (iv), testing if the CTLs generated against the optimized epitope also recognize its cognate native epitope, and selecting those for which the test is positive.

In this method, the appropriate models which can be used in steps (ii) and (iv) are as described above. In step (v), the cross-recognition can be performed by any method known by the skilled artisan, for example as described in the experimental part.

As disclosed in the experimental part below, the inventors have identified in different tumor associated antigens (hTERT, EphA2, MAGE or Her2/neu), a number of putative HLA-A*2402-restricted cryptic epitopes. When testing the immunogenicity of these epitopes, one of them proved to be immunogenic. The inventors have selected the peptides disclosed in Table 2 below, which are confirmed HLA-A*2402-restricted cryptic epitopes. The peptides are part of the present invention.

TABLE 2

Selected confirmed cryptic HLA-A*2402 restricted peptides

| Peptide | Sequence | SEQ ID |
|---|---|---|
| TERT 403 | PYGVLLKTH | ID N° 1 |
| TERT 770 | PYMRQFVAH | ID N° 2 |
| HER 780 | PYVSRLLGI | ID N° 3 |
| EphA2 47 | PYGKGWDLM | ID N° 4 |
| EphA2 502 | TYLVQVQAL | ID N° 5 |
| EphA2 817 | PYWELSNHE | ID N° 6 |
| Her2/neu 922 | PYDGIPARE | ID N° 7 |
| MAGE 261 | RYEFLWGPR | ID N° 8 |
| Her2/neu 300 | PYNYLSTDV | ID N° 9 |

The present invention also pertains to optimized peptides derived from the cryptic peptides of SEQ ID Nos: 1 to 9, by a method according to the invention. Preferred examples of optimized peptides are KYGVLLKTL (SEQ ID No: 11), RYMRQFVAL (SEQ ID No: 12), RYVSRLLGI (SEQ ID No: 13), RYGKGWDLL (SEQ ID No: 14), RYLVQVQAL (SEQ ID No: 15), RYWELSNHL (SEQ ID No: 16). Among these peptides, SEQ ID No: 13 and SEQ ID No: 15 have been derived from the cryptic HLA-A*2402-restricted epitopes of SEQ ID NOs: 3 and 5, respectively, by substitution of their N-terminal amino-acid with a R. The peptides of SEQ ID Nos: 11, 12, 14 and 16 have been derived from the peptides of SEQ ID Nos: 1, 2, 4 and 6, respectively, by substituting their N-terminal amino-acid with an R or a K and their C-terminal amino-acid with a L.

Polyspecific tumor vaccination offers a broader control of tumor cells than monospecific vaccination, thereby reducing the risk of emergence of immune escape variants. In most cases, immunotherapy is then more efficient when targeting several epitopes than when targeting only one epitope, provided the tumour is known to express all targeted antigens. The inventors have previously described a polypeptide composed of HLA-A*0201 restricted optimized cryptic peptides derived from three different universal tumor antigens (TERT$_{988Y}$, HER-2/neu$_{402Y}$ and MAGE-A$_{248V9}$), named Vx-006 (WO 2007/073768). Vx-006 is able to induce a polyspecific CD8 cell response both in vivo in HLA-A*0201 transgenic HHD mice and in vitro in humans, whereas the mixture of TERT$_{988Y}$, HER-2/neu$_{402Y}$ and MAGE-A$_{248V9}$ peptides failed to induce a trispecific response. Hence, a chimeric polypeptide comprising several epitopes can be more efficient than a mere mixture of the same epitopes to trigger a response against more than one epitope. Depending on the context, a chimeric polypeptide comprising a repetition of one single epitope can also trigger a stronger response against said epitope than a peptide consisting of said epitope. Indeed, a polypeptide organization (either with several different epitopes or with a repetition of one single epitope) can produce new junctional epitopes, especially CD4 restricted epitopes, able to optimize the targeted peptide(s)-specific immune response. Moreover, when free peptides are subcutaneously injected, peptides bind directly to MHC molecules of every cells present at the site of injection. As polypeptides need to be processed, vaccination with polypeptides is more efficient to target antigenic peptides to professional Antigenic Presenting Cells (APC) as Dendritic Cells.

A further aspect of the invention is hence a chimeric polypeptide, comprising one, two, three or more HLA-A*2402-restricted cryptic epitopes or one, two, three or more optimized immunogenic HLA-A*2402-restricted epitopes as described above. In a chimeric polypeptide according to the invention, the epitopes can be different from each other, and/or the same epitope can be repeated several times.

It is to be noted that when several epitopes specific for the same HLA molecule are used together, either in a mix or in a chimeric polypeptide, the epitopes are in competition for the binding to the corresponding HLA molecule. Contrarily, by using a mix of different HLA-restricted epitopes (HLA-A*0201, HLA-A*2402, HLA-B*0702 or others), or a chimeric polypeptide comprising the same different HLA-restricted epitopes, there will be no competition for HLA binding, and a polyspecific response will be obtained with certainty, provided all the HLA molecules are expressed in the vaccinated individual.

In a chimeric polypeptide according to the invention, HLA-A*2402-restricted cryptic or optimized immunogenic epitopes described above can hence be advantageously associated to previously described HLA-A*0201 (WO 02/02716) and/or HLA-B*0702 peptides (WO 2008/010010 and WO 2008/010098), or to immunogenic epitopes derived from previously described tumor associated antigens, comprising CEA, PRAME, Tyrosinase, TRAG-3, NY-Eso-1, P53, Muc-1, PSA/PSMA, survivin, Melan-A/MART-1, TRP-1, TRP-2, WT1, EphA1, EphA2, EphA3, EphA4, G250/MN/CAIX, STEAP, alphafoetoprotein, RAGE-1, PAGE-1. Of course, a polyallelic peptides mix, comprising at least a peptide according to the present invention and one different HLA-restricted epitope (HLA-A*0201, HLA-A*2402, HLA-B*0702 or others), is also part of the present invention.

Examples of cryptic epitopes which can advantageously be combined to HLA-A*2402-restricted cryptic epitopes (either in a mix or in a chimeric polypeptide), as well as examples of optimized immunogenic epitopes which can advantageously be combined to optimized immunogenic HLA-A*2402-restricted epitopes, are described in Table 3 below. Of course, these lists are not limitative.

TABLE 3 epitopes which can be combined to HLA-A*2402-restricted epitopes in chimeric polypeptides according to the invention

HLA-A*0201

| Antigen | Native peptide | | Optimized peptide | | |
|---|---|---|---|---|---|
| | Sequence | No | Name | Sequence | No |
| Mart-1$_{27}$ | AAGIGILTV | 23 | Mart-1$_{27Y1}$ | YAGIGILTV | 24 |
| Mart1$_{26}$ | EAAGIGILTV | 25 | Mart1$_{26L27}$ | ELAGIGILTV | 26 |
| Gp100$_{177}$ | AMLGTHTMEV | 27 | Gp100$_{177Y1}$ | YMLGTHTMEV | 28 |
| Gp100$_{178}$ | MLGTHTMEV | 29 | Gp100$_{178Y1}$ | YLGTHTMEV | 30 |
| Gp100$_{154}$ | KTWGQYWQV | 31 | Gp100$_{154Y1}$ | YTWGQYWQV | 32 |
| | | | Gp100$_{154M155}$ | KMWGQYWQV | 33 |
| Gp100$_{570}$ | SLADTNSLAV | 34 | Gp100$_{570Y1}$ | YLADTNSLAV | 35 |
| Gp100$_{209}$ | TDQVPFSV | 36 | Gp100$_{209Y1}$ | YDQVPFSV | 37 |
| | | | Gp100$_{209M210}$ | YMQVPFSV | 38 |
| Gp100$_{476}$ | VLYRYGSFSV | 39 | Gp100$_{476Y1}$ | YLYRYGSFSV | 40 |
| Gp100$_{457}$ | LLDGTATLRL | 41 | Gp100$_{457Y1}$ | YLDGTATLRL | 42 |
| HER-2/neu$_{799}$ | QLMPYGCLL | 43 | HER-2/neu$_{799Y1}$ | YLMPYGCLL | 44 |
| HER-2/neu$_{369}$ | KIFGSLAFL | 45 | HER-2/neu$_{369Y1}$ | YIFGSLAFL | 46 |
| HER-2/neu$_{789}$ | CLTSTVQLV | 47 | HER-2/neu$_{789Y1}$ | YLTSTVQLV | 48 |
| HER-2/neu$_{48}$ | HLYQGCQW | 49 | HER-2/neu$_{48Y1}$ | YLYQGCQW | 50 |
| HER-2/neu$_{773}$ | VMAGVGSPYV | 51 | HER-2/neu$_{773Y1}$ | YMAGVGSPYV | 52 |
| HER-2/neu$_{5}$ | ALCRWGLL | 53 | HER-2/neu$_{5Y1}$ | YLCRWGLL | 54 |
| HER-2/neu$_{851}$ | VLVKSPNHV | 55 | HER-2/neu$_{851Y1}$ | YLVKSPNHV | 56 |
| HER-2/neu$_{661}$ | ILLVVVLGV | 57 | HER-2/neu$_{661Y1}$ | YLLVVVLGV | 58 |
| HER-2/neu$_{650}$ | PLTSIISAV | 59 | HER-2/neu$_{650Y1}$ | YLTSIISAV | 60 |
| HER-2/neu$_{466}$ | ALIHHNTHL | 61 | HER-2/neu$_{466Y1}$ | YLIHHNTHL | 62 |
| HER-2/neu$_{402}$ | TLEEITGYL | 63 | HER-2/neu$_{402Y1}$ | YLEEITGYL | 64 |
| HER-2/neu$_{391}$ | PLQPEQLQV | 65 | HER-2/neu$_{391Y1}$ | YLQPEQLQV | 66 |
| HER-2/neu$_{971}$ | ELVSEFSRM | 67 | HER-2/neu$_{971Y1}$ | YLVSEFSRM | 68 |
| EphA2$_{61}$ | DMPIYMYSV | 69 | EphA2$_{61Y1}$ | YMPIYMYSV | 70 |
| HER2$_{911}$ | TVWELMTFGA | 71 | HER$_{911Y1V10}$ | YVWELMTFGV | 74 |
| HER4$_{911}$ | TIWELMTFGG | 72 | | | |
| HER1$_{911}$ | TVWELMTFGS | 73 | | | |
| HER2$_{722}$ | KVKVLGSGA | 75 | HER$_{722Y1V9}$ | YVKVLGSGV | 79 |
| HER3$_{722}$ | KLKVLGSGV | 76 | | | |
| HER4$_{722}$ | RVKVLGSGA | 77 | | | |
| HER1$_{722}$ | KIKVLGSGA | 78 | | | |
| HER2$_{845}$ | DLAARNVLV | 80 | HER$_{845Y1}$ | YLAARNVLV | 82 |
| HER3$_{845}$ | NLAARNVLL | 81 | | | |
| HER2$_{904}$ | DVWSYGVTV | 83 | HER$_{904Y1}$ | YVWSYGVTV | 85 |
| HER4$_{904}$ | DVWSYGVTI | 84 | | | |
| HER2$_{933}$ | DLLEKGERL | 86 | HER$_{933Y1}$ | YLLEKGERL | 88 |
| HER1$_{933}$ | SILELKGERL | 87 | | | |
| HER2$_{945}$ | PICTIDVYMI | 89 | HER$_{945Y1}$ | YICTIDVYMV | 93 |
| HER3$_{945}$ | QICTIDVYMV | 90 | | | |
| HER4$_{945}$ | PICTIDVYMV | 91 | | | |
| HER1$_{945}$ | PICTIDVYKI | 92 | | | |
| MAGE-A$_{248G9}$ | YLEYRQVPG | 94 | MAGE-A$_{248V9}$ | YLEYRQVPV | 96 |
| MAGE-A$_{248D9}$ | YLEYRQVPD | 95 | | | |
| TERT$_{988}$ | DLQVNSLQTV | 97 | TERT$_{988Y1}$ | YLQVNSLQTV | 98 |
| TERT$_{572}$ | RLFFYRKSV | 99 | TERT$_{572Y1}$ | YLFFYRKSV | 100 |

HLA-B*0702

| Native peptide | | | Optimized peptide | | |
|---|---|---|---|---|---|
| Name | Sequence | No | Name | Sequence | No |
| TERT$_{444}$ | FPRRLVQLL | 101 | TERT$_{444A1}$ | APRRLVQLL | 102 |
| CEA$_{188/554}$ | SPRLQLSNG | 103 | CEA$_{188/554L9}$ | SPRLQLSNL | 104 |
| HER-2/neu$_{1069}$ | APRSPLAPS | 105 | HER-2/neu$_{1069L9}$ | APRSPLAPL | 106 |
| HER-2/neu$_{870}$ | SPKANKEIL | 107 | HER-2/neu$_{760A1}$ | APKANKEIL | 108 |
| HER-2/neu$_{246}$ | GPKHSDCLA | 109 | HER-2/neu$_{246A1}$ | APKHSDCLA | 110 |

The skilled artisan can chose any known technique to produce such polypeptides. For example, the polypeptide can be obtained by chemical synthesis, or by using the technology of genetic engineering (Velders et al., 2001).

Another object of the present invention is an isolated nucleic acid molecule designed to cause the expression of a cryptic HLA-A*2402-restricted epitope, or of an optimized immunogenic HLA-A*2402-restricted epitope, or of a chimeric polypeptide as above-described. By "designed to cause the expression of" a peptide is herein meant that said peptide is expressed as such, isolated from the whole antigen from which its sequence has been selected (and, in appropriate cases, optimized as above-described), when the nucleic acid is introduced in an appropriate cell. The region encoding the epitope or chimeric polypeptide will typically be situated in the polynucleotide under control of a suitable promoter. Bacterial promoters will be preferred for expression in bacteria, which can produce the polypeptide either in vitro, or, in particular circumstances, in vivo. An example of bacterium that can be used to produce a peptide or polypeptide according to the invention, directly in vivo, is *Listeria monocytogenes*, which is a facultative intracellular bacterium that enters professional antigen-presenting cells by active phagocytosis (Paterson and Maciag, 2005). Alternatively, a nucleic acid according to the invention can be administered directly, using an appropriate vector. In this case, a tissue-specific, a strong constitutive, or an endogenous promoter can be used to control the peptide expression. Suitable vector systems include naked DNA plasmids, liposomal compositions to enhance delivery, and viral vectors that cause transient expression. Examples of viral vectors are adenovirus or vaccinia virus vectors and vectors of the herpes family, especially in a non-replicative form.

The present invention also pertains to a pharmaceutical composition comprising at least, as an active principle, an HLA-A*2402-restricted cryptic epitope as above-described, or an optimized immunogenic epitope polypeptide as mentioned above, or a chimeric polypeptide according to the invention, or a nucleic acid encoding any of these, and/or a vector carrying said nucleic acid. Formulation of pharmaceutical compositions will accord with contemporary standards and techniques. Medicines intended for human administration will be prepared in adequately sterile conditions, in which the active ingredient(s) are combined with an isotonic solution or other pharmaceutical carrier appropriate for the recommended therapeutic use. Suitable formulations and techniques are generally described in the latest edition of Remington's Pharmaceutical Sciences (Maack Publishing Co, Easton Pa.).

In particular, a HLA-A*2402-restricted epitope or a chimeric polypeptide or a nucleic acid according to the invention can be used for the preparation of a composition for preventive or curative immunotherapy, especially, for antiviral or anti-cancer immunotherapy.

In a particular embodiment, a pharmaceutical composition according to the invention is a vaccine. In this latter case, the components described above can be combined with an adjuvant to potentiate the immune response. Classic adjuvants include oil emulsions, like Incomplete Freund's Adjuvant or Montanide, and adherent surfaces such as alum. Adjuvants that recruit and activate dendritic cells particularly via TLR (such as bacterial DNA or bacterial membrane derived proteins) or help elicit cytotoxic T cells are especially useful. Other factors that otherwise boost the immune response or promote apoptosis or elimination of cancer cells can also be included in the composition, such as IL-2 or IL-12 cytokines or GM-CSF.

Multiple doses and/or different combinations of the immunogenic compositions of this invention can be packaged for distribution separately or together. Each composition or set of compositions, such as the kits of parts described below, can be accompanied with written instructions regarding the use of the composition or combination for eliciting an immune response and/or for the treatment of cancer.

In a previous patent application (WO 2006/120038), the Applicant has described a vaccination protocol which enables the initiation and maintenance of a T cell response targeting sub-dominant/cryptic epitopes. The results reported in WO 2006/120038 demonstrate that injection of a native peptide corresponding to a sub-dominant/cryptic epitope, following vaccination with its cognate optimized peptide, can maintain the immune response initiated by said optimized peptide.

According to the invention, a HLA-A*2402-restricted cryptic epitope can hence be used for the preparation of a medicinal composition for maintaining the CTL immune response initiated by its cognate optimized peptide. An immunogenic peptide having an optimized immunogenic HLA-A*2402-restricted epitope sequence derived from a HLA-A*2402-restricted cryptic epitope can also be used, for the preparation of a medicinal composition for initiating a CTL immune response against said HLA-A*2402-restricted cryptic epitope. The present invention also encompasses a method for vaccinating a patient against a tumoral or viral antigen, wherein said method comprises a first step of vaccination with an optimized immunogenic peptide cognate to a native HLA-A*2402-restricted cryptic epitope of said antigen, followed by a second step of vaccination with said native peptide. In such a method, the first step and/or the second step can be performed by using a chimeric polypeptide comprising one, two, three or more optimized or cryptic peptides as above-described, instead of single-epitope peptides.

The invention also pertains to a kit of parts comprising, in separate formulations or containers (vials, tubes, etc.):

(i) a first peptide comprising a sequence of a HLA-A*2402-restricted cryptic epitope, and (ii) a second peptide comprising a sequence corresponding to an optimized immunogenic epitope cognate to the cryptic epitope recited in (i).

Examples of peptides which can be part of a kit according to the invention are the peptides of SEQ ID NOs: 1 to 6, which can constitute the first peptide, the second peptide being then derived from said first peptide by a method for increasing its immunogenicity, as described above. Preferred kits according to the invention can hence comprise peptides of SEQ ID Nos: 1 and 11 (in separate containers), or peptides of SEQ ID Nos: 2 and 12 (in separate containers), or peptides of SEQ ID Nos: 3 and 13 (in separate containers), or peptides of SEQ ID Nos: 4 and 14 (in separate containers), or peptides of SEQ ID Nos: 5 and 15 (in separate containers), or peptides of SEQ ID Nos: 6 and 16 (in separate containers).

Other kits of parts according to the invention comprise at least one chimeric polypeptide. In this embodiment, the kit also comprises at least a peptide cognate to one of the epitopes comprised in the chimeric polypeptide, wherein said cognate peptide is either isolated or included in another chimeric polypeptide.

Several preferred variants of such kits are contemplated: in a first embodiment, the kit comprises, in separate formulations, a first chimeric polypeptide comprising one, two, three or more HLA-A*2402-restricted cryptic epitopes, and a second chimeric polypeptide corresponding to its cognate HLA-A*2402-restricted immunogenic chimeric polypeptide (which means that it comprises optimized HLA-A*2402-restricted immunogenic epitopes cognate to the cryptic epitopes comprised in the first chimeric polypeptide). In a second embodiment, the kit comprises one, two, three or more peptides corresponding to distinct HLA-A*2402-restricted cryptic epitopes, wherein said peptides are either mixed in one single formulation, or separated in several formulations and, in a separate formulation, a chimeric polypeptide comprising the optimized HLA-A*2402-restricted immunogenic epitopes cognate to said cryptic peptides.

As mentioned above, a polyallelic stimulation (i.e., using epitopes specific for different HLA molecules) can advantageously be performed to obtain a polyspecific response. Accordingly, preferred embodiments of the kits according to the invention comprise, in separate containers:

(i) a polyallelic peptides mix or a polyallelic chimeric polypeptide, comprising at least a HLA-A*2402-restricted cryptic epitope as described above and at least one different HLA-restricted cryptic epitope, and (ii) a polyallelic peptides mix or a polyallelic chimeric polypeptide, comprising at least a HLA-A*2402-restricted immunogenic epitope cognate to the HLA-A*2402-restricted cryptic epitope recited in (i), and at least another immunogenic epitope cognate to the other cryptic epitope recited in (i).

Alternatively, the kits according to the invention can comprise, instead of at least part the peptides or chimeric polypeptides, nucleic acid(s) encoding said peptides or chimeric polypeptides. In this case, the nucleic acid(s) is(are) as above-described.

In the following description of some specific kits according to the invention, mention will be made only of the peptides (native or optimized) included therein; it is understood that chimeric polypeptide(s) (comprising native cryptic epitopes or optimized epitopes) can be enclosed in the kits instead of single-epitope peptides, and that nucleic acid(s) can also be included in addition or instead of at least part of said peptides or chimeric polypeptides.

In a particular embodiment of the invention, the kit is a vaccination kit, wherein said first (native) and second (cognate optimized) peptides are in separate vaccination doses. In a preferred embodiment, the vaccination kit comprises 2 or 3 doses of optimized peptide, and 3, 4, 5 or 6 doses of native peptide. A particular vaccination kit according to the invention is adapted for the first vaccination sequence of 6 injections, and comprises 2 or 3 doses of optimized peptide, and 4 or 3 doses of native peptide. In case of long-lasting diseases, it is preferable to maintain the level of immunity obtained after this primo-vaccination, by regular recalls. This can be done, for example, by injections performed every 1 to 6 months. Therefore, complementary kits, comprising at least 2 doses, and up to 40 or 50 doses of native peptide, are also part of the present invention. Alternatively, the vaccination kit can comprise 2 to 3 doses of optimized peptide, and 3 to 40 or up to 50 doses of native peptide. Of course, said native and optimized peptides present in the kit are as described above.

Each dose comprises between 0.1 and 10 mg of peptide, preferably from 1 to 5 mg, or between 1 and 20 mg of polypeptide. In a preferred embodiment, each dose is formulated for subcutaneous injection. For example, each dose can be formulated in 0.3 to 1.5 ml of an emulsion of aqueous solution emulsified with Montanide ISA51, used as an adjuvant. The skilled artisan can choose any other adjuvant(s) in place of (or in addition to) Montanide ISA51. In a particular embodiment, the doses are in the form of an aqueous solution. Alternatively, the doses can be in the form of a lyophilized peptide, for extemporaneous preparation of the liquid solution to be injected. Other possible components of said kits are one or several adjuvants, to be added to the peptide compositions before administration, and a notice describing how to use said kits.

The invention is further illustrated by the following figures and examples.

LEGENDS OF FIGURES

FIG. 1: Panels 1A-1F of FIG. 1 show immunogenicity of HLA-A*2402 cryptic peptides. HLA-A*2402 transgenic mice were vaccinated with the cryptic peptides following the described protocol and generated CTL were tested against T2-A24 targets loaded with peptide as indicated (NR non relevant peptide). Percentage of specific lysis was determined as: Lysis=(Experimental Release−Spontaneous Release)/(Maximal Release−Spontaneous Release)×100. Four CTL dilutions, corresponding to four CTL/target cells ratio were tested.

Figure 2:
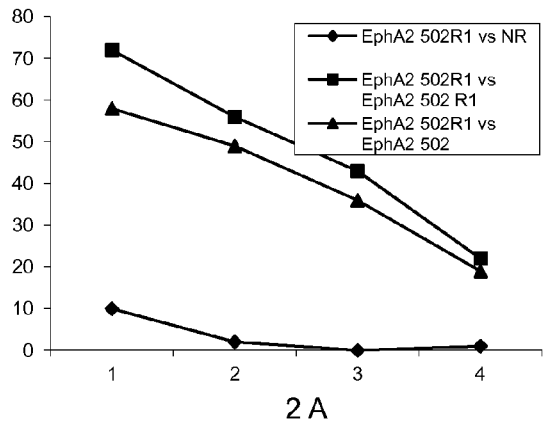
Figure 2:
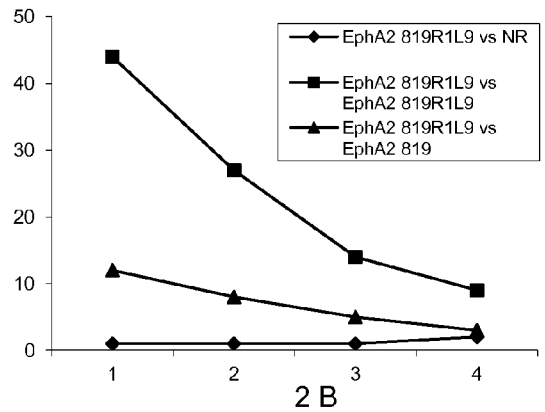
Figure 2:
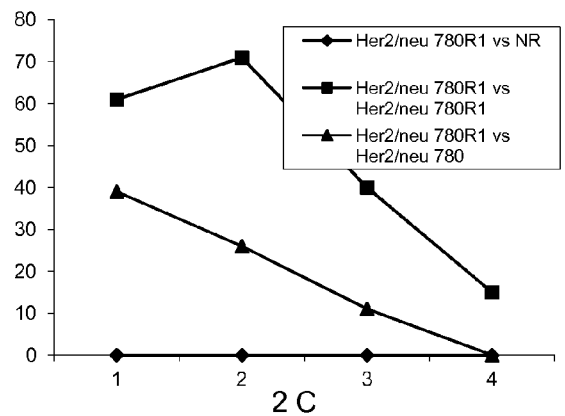
Figure 2:
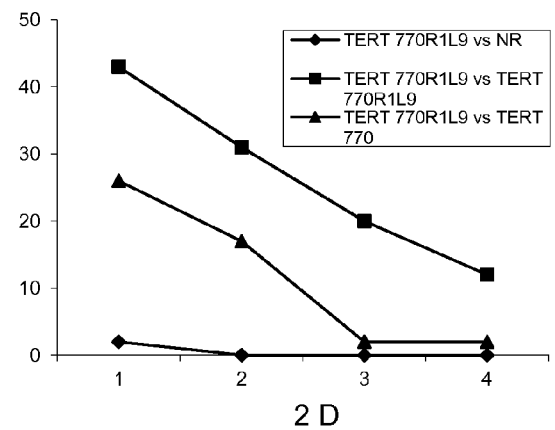
Figure 2:
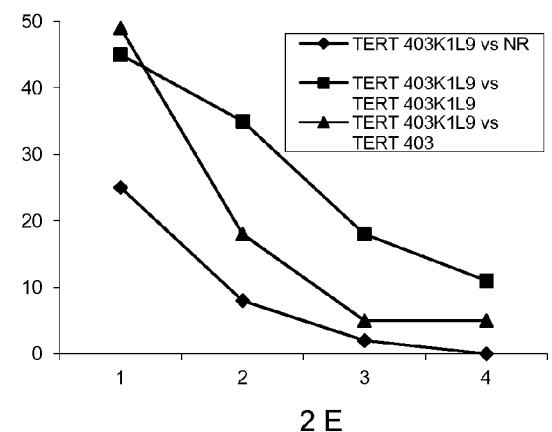
Figure 2:
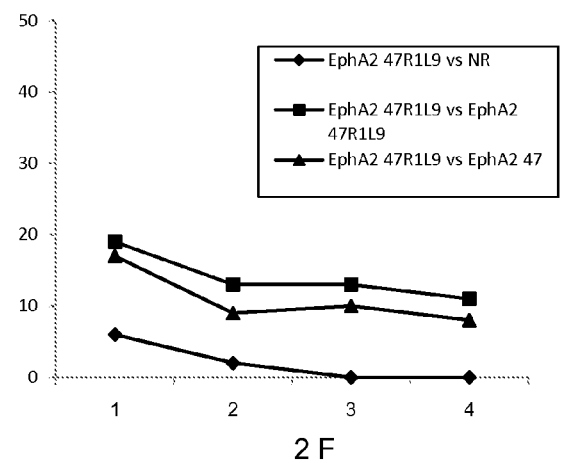

FIG. 2: Panels 2A-2F of FIG. 2 show immunogenicity of HLA-A*2402 restricted optimized cryptic peptides. HLA-A*2402 transgenic mice were vaccinated with the optimized peptide following the described protocol and generated CTL were tested against T2-A24 targets loaded with the optimized (immunogenicity), the corresponding native (native peptide cross recognition) or an irrelevant (NR) peptide as indicated. Percentage of specific lysis was determined as: Lysis=(Experimental Release−Spontaneous Release)/(Maximal Release−Spontaneous Release)×100. Four CTL dilutions, corresponding to four CTL/target cells ratio were tested.

EXAMPLES

The examples have been performed using the following materials and methods:esd

Transgenic Mice.

The transgenic mice used in the described experiments were obtained by crossing HLA-A24 transgenic mice previously described (Barra et al., 1993) and H2 Kb$^-$ H2 Db$^-$ knock out mice, transgenic for both human β2 microglobulin and CD8α chain (Perarnau et al., 1999).

Peptides.

Peptides were synthesized by Epytop (Nîmes, France).

Cells.

HLA-A*2402 transfected human TAP negative T2-A24 cells were previously described (Miyahara et al., 2005), and were provided by Dr. Lemonnier (Institut Pasteur, Paris, France). All cell lines were grown in FCS 10% supplemented RPMI1640 culture medium.

Measurement of Peptide Relative Affinity to HLA-A*2402.

The protocol used has been described previously (Rohrlich et al., 2003). Briefly, T2-A24 cells were incubated at 37° C. for 16 hours with peptides concentrations ranging from 100 µM to 0.1 µM, and then stained with 0041HA monoclonal antibody (mAb)(One Lambda, Inc.) to quantify the surface expression of HLA-A*2402. For each peptide concentration, the HLA-A*2402 specific staining was calculated as the percentage of staining obtained with 100 µM of the reference peptide standard A24 (AYIDNYNKF, SEQ ID NO: 111). The relative affinity (RA) was determined as: RA=(Concentration of each peptide that induces 30% of HLA-A*2402-expression/Concentration of the reference peptide that induces 30% of HLA-A*2402 expression).

CTL Induction In Vivo in HLA-A*2402 Transgenic Mice.

Mice were injected subcutaneously with 100 µg of peptide emulsified in Incomplete Freund's Adjuvant (IFA) in the presence of 150 µg of the I-A$^b$ restricted HBVcore$_{128}$ T helper epitope (TPPAYRPPNAPIL, SEQ ID NO: 112). After 15 days, 5×10$^7$ spleen cells were stimulated twice in vitro with peptide (10 µM), at 6 days interval. On day 13 of culture, the bulk responder populations were tested for specific cytotoxicity against target cells expressing HLA-A*2402 and loaded with the same peptide.

Cross-Recognition Assay.

Mice were injected subcutaneously with 100 µg of optimized peptide emulsified in Incomplete Freund's Adjuvant (IFA) in the presence of 150 µg of the I-A$^b$ restricted HBV-core$_{128}$ T helper epitope (TPPAYRPPNAPIL, SEQ ID NO: 112). After 15 days, 5×10$^7$ spleen cells were stimulated firstly in vitro with the optimized peptide (10 µM), and secondly on day 6 of culture with the corresponding native peptide. On day 13, the bulk responder populations were tested for specific cytotoxicity against targets cells expressing HLA-A*2402 and loaded with the optimized, the native or an irrelevant peptide.

Cytotoxic Assay.

Targets were labelled with 100 µCi of Cr$^{51}$ for 60 min, plated in 96-well V-bottomed plates (3×10$^3$ cell/well in 100 µL of RPMI 1640 medium) and, when necessary, pulsed with optimized or native peptides (1 µM) at 37° C. for 2 hours. Four dilutions of effector cells were then added in the wells and incubated at 37° C. for 4 hours. Percentage of specific lysis was determined as: Lysis=(Experimental Release−Spontaneous Release)/(Maximal Release−Spontaneous Release)×100.

Example 1

Affinity and Immunogenicity of Selected Cryptic Peptides

The inventors have selected 10 native peptides according to the selection method described above. First, seven peptides were tested for their capacity to bind HLA-A*2402 molecules. All but two peptides were not or weakly able to bind to the HLA-A*2402.

TABLE 4

HLA-A*2402 affinity of cryptic peptides.
RA = Relative Affinity = (Concentration of each peptide that induces 30% of HLA-A*2402-expression/Concentration of the reference peptide that induces 30% of HLA-A*2402 expression), (−) means RA > 100, (+/−) 10 < RA < 100, (+) 5 < RA < 10, (++) RA < 5, ND: not determined

| Antigen/position | Sequence | RA | SEQ ID No |
|---|---|---|---|
| TERT 403 | PYGVLLKTH | − | 1 |
| TERT 770 | PYMRQFVAH | +/− | 2 |
| Her2/neu 780 | PYVSRLLGI | +/+ | 3 |
| EphA2 47 | PYGKGWDLM | ND | 4 |
| EphA2 502 | TYLVQVQAL | ND | 5 |
| EphA2 817 | PYWELSNHE | ND | 6 |
| Her2/neu 922 | PYDGIPARE | − | 7 |
| MAGE 261 | RYEFLWGPR | − | 8 |
| Her2/neu 300 | PYNYLSTDV | − | 9 |
| Her2/neu 802 | PYGCLLDHV | + | 10 |

HLA-A24 transgenic mice were then vaccinated with the selected peptides, and fifteen days later, their spleen cells were in vitro stimulated twice at 6 days intervals with the peptide. Peptide-specific CTLs were detected in mice vaccinated with control high affinity peptides selected as having primary Y2 and/or C-terminal anchor motifs (data not shown). Native peptides, which were not able to bind to the HLA-A*2402 were shown to be also non immunogenic (FIG. 1) and Her2/neu 802, which binds to the HLA-A*2402, was shown to be immunogenic in transgenic mice. This confirms that there is a correlation between binding affinity and immunogenicity for the HLA-A*2402 restricted peptides.

Nevertheless, as Her2/neu 780 strongly binds to HLA-A*2402 but is finally non immunogenic, the inventors decided to select native peptides only on their incapacity to induce a specific immune response in HLA-A24 transgenic mice. Finally, only one native peptide selected according to the described selection method was able to generate a specific immune response in HLA-A*2402 transgenic mice, confirming that the described method allows to efficiently select putative cryptic peptides. Immunogenicity of selected native peptides is shown in table 5.

TABLE 5

HLA-A*2402 immunogenicity of selected cryptic peptides.
(−) means that none of the mice vaccinated with the corresponding native peptides develops a specific immune response, (+) that less to 50% of vaccinated mice responded, (++) that more that 50% responded.
ND: not determined

| Antigen/position | Sequence | Immunogenicity | SEQ ID No |
|---|---|---|---|
| TERT403 | PYGVLLKTH | − | 1 |
| TERT770 | PYMRQFVAH | − | 2 |
| Her2/neu 780 | PYVSRLLGI | − | 3 |
| EphA2 47 | PYGKGWDLM | − | 4 |
| EphA2 502 | TYLVQVQAL | − | 5 |
| EphA2 817 | PYWELSNHE | − | 6 |
| Her2/neu 922 | PYDGIPARE | ND | 7 |
| MAGE 261 | RYEFLWGPR | − | 8 |
| Her2/neu 300 | PYNYLSTDV | − | 9 |
| Her2/neu 802 | PYGCLLDHV | ++ | 10 |

Example 2

Enhancement of Immunogenicity of the Selected Cryptic Peptides

To enhance HLA-A*2402 affinity and consequently immunogenicity of low affinity peptides with the HLA specific anchor motifs, it was necessary to identify unfavourable secondary anchor motifs and substitute them with favourable motifs. These substitutions must however preserve the conformation of the peptide segment which interacts with the TCR (position 4 to position 8). The interest was, therefore, focused on secondary anchor position 1. Positively charged amino acids (lysine (K) or arginine (R)) are favourable motifs at position 1 whereas a proline (P) is an unfavourable amino acid.

Moreover, as shown in table 6 below, more than 50% of HLA-A*2402 CD8 epitope identified both in tumors and HIV cells, have a leucine (L) in C-terminal position. The inventors hence decided to use L as the C terminal modification to enhance immunogenicity of peptides preferentially having an unfavourable amino acids in this position (aspartic or glutamic acid (D,E), glycine (G), histidine (H), glutamine (Q), lysine (K), proline (P) or arginine (R)).

TABLE 6

Tumor and HIV derived HLA-A*2402 restricted epitopes

| Antigen | Sequence | No | reference |
|---|---|---|---|
| Beta-catenin | SYLDSGIHF | 113 | www.cancerimmunity.org/peptidedatabase/mutation.htm |
| HM-HN-1 | NYNNFYRFL | 114 | www.cancerimmunity.org/peptidedatabase/tumorspecific.htm |
| KM-HN-1 | EYSKECLKEF | 115 | www.cancerimmunity.org/peptidedatabase/differentiation.htm |

TABLE 6-continued

Tumor and HIV derived HLA-A*2402 restricted epitopes

| Antigen | Sequence | No | reference |
|---|---|---|---|
| KM-HN-1 | EYLSLSDKI | 116 | www.cancerimmunity.org/peptidedatabase/overexpressed.htm |
| MAGE-A2 | EYLQLVFGI | 117 | |
| MAGE-A3 | VAELVHFLL | 119 | |
| MAGE-A4 | NYKRVFPVI | 120 | |
| SAGE | LYATVIHDI | 121 | |
| CEA | QYSWFVNGTF | 122 | |
| CEA | TYACFVSNL | 123 | |
| gp100/Pmel17 | VYFFLPDHL | 124 | |
| OA1 | LYSACFWWL | 125 | |
| tyrosinase | AFLPWHRLF | 126 | |
| Ep-CAM | RYQLDPKFI | 127 | |
| Her2/neu | TYLPTNASL | 128 | |
| PRAME | LYVDSLFFL | 129 | |
| PSMA | NYARTEDFF | 130 | |
| RNF43 | NSQPVWLCL | 131 | |
| TERT | TYVPLLGSL | 132 | Ref peptides TERT |
| TERT | CYGDMENKL | 133 | |
| TERT | AVQVCGPPL | 134 | |
| WT1 | CMTWNQMNL | 135 | |
| p17 | HYMLKHLVW | 136 | hiv-web.lanl.gov/content/immunology/tables/ctl_summary.html |
| p17 | KYKLKHIVW | 137 | |
| p17 | LYNTVATL | 138 | |
| p17 | LYCVHQKI | 139 | |
| p17-p24 | NYPIVQNL | 140 | |
| p24 | EIYKRWIIL | 141 | |
| p24 | IYKRWIIL | 142 | |
| p24 | IYKRWIILGL | 143 | |
| p2p7p1p6 | LYPLASLRSL | 144 | |
| RT | DAYFSVPL | 145 | |
| RT | VYYDPSKDL | 146 | |
| RT | IYQEPFKNL | 147 | |
| Integrase | GYIEAEVI | 148 | |
| gp160 | LFCASDAKAY | 149 | |
| gp160 | RYLRDQQL | 150 | |
| gp160 | RYLKDQQLL | 151 | |
| gp160 | RYLRDQQLL | 152 | |
| gp160 | RYLRDQQLLGI | 153 | |
| gp160 | YLKDQQLL | 154 | |
| gp160 | YLRDQQLL | 155 | |
| gp160 | WYIKIFIMI | 156 | |
| gp160 | SYRRLRDLL | 157 | |
| Nef | TYKAAVDL | 158 | |
| Nef | HSQRRQDIL | 159 | |
| Nef | RQDILDLWI | 160 | |
| Nef | GYFPDWQNY | 161 | |
| Nef | NYTPGPGVRY | 162 | |
| Nef | RYPLTFGW | 163 | |
| Nef | RYPLTFGWCF | 164 | |
| Nef | FYPLTFGWCY | 165 | |
| Nef | DSRLAFHHM | 166 | |
| Nef | AFHHVAREL | 167 | |

Optimized peptides were tested for their immunogenicity (table 7, FIG. 2), showing that the chosen modification enhances the capacity to induce specific immune response in HLA-A24 transgenic mice for six native peptides. HLA-A24 transgenic mice vaccinated with the TERT 403KIL9, TERT 770R1L9, HER 780R1, EphA2 47R1L9, EphA2 502R1 and EphA2 817R1L9 peptides, developed peptide specific CTLs.

Importantly, CTLs generated in mice vaccinated with optimized peptides recognized target cells loaded with the corresponding native peptide (FIG. 2).

TABLE 7

Native and modified peptides immunogenicity and native peptide cross recognition. (-) means that none of the mice vaccinated with the corresponding native peptides develops a specific immune response, (+) that less to 50% of vaccinated mice responded, (++) that more that 50% responded. (X/Y) means that X mice develop a specific response for a total of Y mice vaccinated. ND: not determined.

| Antigen/position | Modification | Sequence | Immunogenicity | Native peptide cross recognition | SEQ ID N° |
|---|---|---|---|---|---|
| TERT 403 | | PYGVLLKTH | -(0/3) | +(3/15) | 1 |
| TERT 403 | K1L9 | KYGVLLKTL | +(4/15) | | 11 |

TABLE 7-continued

Native and modified peptides immunogenicity and native peptide cross recognition.
(-) means that none of the mice vaccinated with the corresponding native peptides
develops a specific immune response, (+) that less to 50% of vaccinated mice
responded, (++) that more that 50% responded. (X/Y) means that X mice develop a
specific response for a total of Y mice vaccinated. ND: not determined.

| Antigen/position | Modification | Sequence | Immunogenicity | Native peptide cross recognition | SEQ ID N° |
|---|---|---|---|---|---|
| TERT 770 | | PYMRQFVAH | -(0/3) | +(5/18) | 2 |
| TERT 770 | R1L9 | RYMRQFVAL | ++(12/18) | | 12 |
| HER 780 | | PYVSRLLGI | -(0/8) | +(3/9) | 3 |
| HER 780 | R1 | RYVSRLLGI | +(4/9) | | 13 |
| EphA2 47 | | PYGKGWDLM | -(0/6) | ++(7/9) | 4 |
| EphA2 47 | R1L9 | RYGKGWDLL | ++(7/9) | | 14 |
| EphA2 502 | | TYLVQVQAL | -(0/3) | ++(2/3) | 5 |
| EphA2 502 | R1 | RYLVQVQAL | ++(3/3) | | 15 |
| EphA2 817 | | PYSELSNHE | -(0/3) | ++(2/3) | 6 |
| EphA2 817 | R1L9 | RYWELSNHL | ++(2/3) | | 16 |
| Her2/neu 922 | | PYDGIPARE | ND | | 7 |
| Her2/neu 922 | R1L9 | RYDGIPARL | -(0/9) | | 17 |
| MAGE 261 | | RYEFLWGPR | -(0/3) | | 8 |
| MAGE 261 | L9 | RYEFLWGPL | -(0/9) | | 18 |
| Her2/neu 300 | | PYNYLSTDV | -(0/3) | | 9 |
| Her2/neu 300 | R1L9 | RYNYLSTDL | -(0/9) | | 19 |

In conclusion, the inventors describe a method to optimize immunogenicity of HLA-A*2402 restricted cryptic peptides. It consists of a) selecting cryptic peptides with Y2 and unfavourable amino acids in secondary anchor position 1 and/or 9; and b) substituting the unfavourable amino acids at the N-terminal position with a positively charged amino acid (R or K) and the C-terminal residue with a L when this later substitution is necessary.

Using these methods of selection/optimization, the inventors also described 6 optimized cryptic peptides that induce specific CTLs in transgenic mice able to recognize cells presenting the corresponding native peptide.

REFERENCES

Bakker, A. B., van der Burg, S. H., Huijbens, R. J., Drijfhout, J. W., Melief, C. J., Adema, G. J. and Figdor, C. G. (1997) Analogues of CTL epitopes with improved MHC class-I binding capacity elicit anti-melanoma CTL recognizing the wild-type epitope. *Int J Cancer*, 70, 302-309.

Barra, C., Gournier, H., Garcia, Z., Marche, P. N., Jouvin-Marche, E., Briand, P., Fillipi, P. and Lemonnier, F. A. (1993) Abrogation of H-2-restricted CTL responses and efficient recognition of HLA-A3 molecules in DBA/2 HLA/A24 responder mice. *J Immunol*, 150, 3681-3689.

Cibotti, R., Kanellopoulos, J. M., Cabaniols, J. P., Halle-Panenko, O., Kosmatopoulos, K., Sercarz, E. and Kourilsky, P. (1992) Tolerance to a self-protein involves its immunodominant but does not involve its subdominant determinants. *Proc Nad Acad Sci USA*, 89, 416-420.

Engelhorn, M. E., Guevara-Patino, J. A., Noffz, G., Hooper, A. T., Lou, O., Gold, J. S., Kappel, B. J. and Houghton, A. N. (2006) Autoimmunity and tumor immunity induced by immune responses to mutations in self. *Nat Med*, 12, 198-206.

Gross, D. A., Graff-Dubois, S., Opolon, P., Cornet, S., Alves, P., Bennaceur-Griscelli, A., Faure, O, Guillaume, P., Firat, H., Chouaib, S., Lemonnier, F. A., Davoust, J., Miconnet, I., Vonderheide, R. H. and Kosmatopoulos, K. (2004) High vaccination efficiency of low-affinity epitopes in antitumor immunotherapy. *J Clin Invest*, 113, 425-433.

Miyahara, Y., Naota, H., Wang, L., Hiasa, A., Goto, M., Watanabe, M., Kitano, S., Okumura, S., Takemitsu, T., Yuta, A., Majima, Y., Lemonnier, F. A., Boon, T. and Shiku, H. (2005) Determination of cellularly processed HLA-A2402-restricted novel CTL epitopes derived from two cancer germ line genes, MAGE-A4 and SAGE. *Clin Cancer Res*, 11, 5581-5589.

Moudgil, K. D., Southwood, S., Ametani, A., Kim, K., Sette, A. and Sercarz, E. E. (1999) The self-directed T cell repertoire against mouse lysozyme reflects the influence of the hierarchy of its own determinants and can be engaged by a foreign lysozyme. *J Immunol*, 163, 4232-4237.

Parkhurst, M. R., Salgaller, M. L., Southwood, S., Robbins, P. F., Sette, A., Rosenberg, S. A. and Kawakami, Y. (1996) Improved induction of melanoma-reactive CTL with peptides from the melanoma antigen gp100 modified at HLA-A*0201-binding residues. *J Immunol*, 157, 2539-2548.

Paterson, Y. and Maciag, P. C. (2005) Listeria-based vaccines for cancer treatment. *Curr Opin Mol Ther*, 7, 454-460.

Perarnau, B., Saron, M. F., San Martin, B. R., Bervas, N., Ong, H., Soloski, M. J., Smith, A. G., Ure, J. M., Gairin, J. E. and Lemonnier, F. A. (1999) Single H2 Kb, H2 Db and double H2 KbDb knockout mice: peripheral CD8+ T cell repertoire and anti-lymphocytic choriomeningitis virus cytolytic responses. *Eur J Immunol*, 29, 1243-1252.

Rohrlich, P. S., Cardinaud, S., Firat, H., Lamari, M., Briand, P., Escriou, N. and Lemonnier, F. A. (2003) HLA-B*0702 transgenic, H-2 KbDb double-knockout mice: phenotypical and functional characterization in response to influenza virus. *Int Immunol*, 15, 765-772.

Rosenberg, S. A., Yang, J. C. and Restifo, N. P. (2004) Cancer immunotherapy: moving beyond current vaccines. *Nat Med*, 10, 909-915.

Ruppert, J., Sidney, J., Celis, E., Kubo, R. T., Grey, H. M. and Sette, A. (1993) Prominent role of secondary anchor residues in peptide binding to HLA-A2.1 molecules. *Cell*, 74, 929-937.

Scardino, A., Gross, D. A., Alves, P., Schultze, J. L., Graff-Dubois, S., Faure, O., Tourdot, S., Chouaib, S., Nadler, L. M., Lemonnier, F. A., Vonderheide, R. H., Cardoso, A. A. and Kosmatopoulos, K. (2002) HER-2/neu and hTERT cryptic epitopes as novel targets for broad spectrum tumor immunotherapy. *J Immunol,* 168, 5900-5906.

Tourdot, S. and Gould, K. G. (2002) Competition between MHC class I alleles for cell surface expression alters CTL responses to influenza A virus. *J Immunol,* 169, 5615-5621.

Valmori, D., Gervois, N., Rimoldi, D., Fonteneau, J. F., Bonelo, A., Lienard, D., Rivoltini, L., Jotereau, F., Cerottini, J. C. and Romero, P. (1998) Diversity of the fine specificity displayed by HLA-A*0201-restricted CTL specific for the immunodominant Melan-A/MART-1 antigenic peptide. *J Immunol,* 161, 6956-6962.

Velders, M. P., Weijzen, S., Eiben, G. L., Elmishad, A. G., Kloetzel, P. M., Higgins, T., Ciccarelli, R. B., Evans, M., Man, S., Smith, L. and Kast, W. M. (2001) Defined flanking spacers and enhanced proteolysis is essential for eradication of established tumors by an epitope string DNA vaccine. *J Immunol,* 166, 5366-5373.

The invention claimed is:

1. An isolated peptide consisting of an immunogenic HLA-A*2402-restricted epitope, wherein said isolated peptide is selected from the group consisting of KYGVLLKTL (SEQ ID NO: 11); RYMRQFVAL (SEQ ID NO: 12); RYVSRLLGI (SEQ ID NO: 13); RYGKGWDLL (SEQ ID NO: 14); RYLVQVQAL (SEQ ID NO: 15); and RYWELSNHL (SEQ ID NO: 16).

2. A chimeric polypeptide, comprising one or more immunogenic HLA-A*2402-restricted epitopes according to claim 1.

3. A kit of parts comprising, in separate containers:
  (i) a first peptide with an amino acid sequence selected from the group consisting of PYGVLLKTH (SEQ ID NO: 1); PYMRQFVAH (SEQ ID NO: 2); PYVSRLLGI (SEQ ID NO: 3); PYGKGWDLM (SEQ ID NO: 4); TYLVQVQAL (SEQ ID NO: 5); PYWELSNHE (SEQ ID NO: 6); PYDGIPARE (SEQ ID NO: 7); RYEFLWGPR (SEQ ID NO: 8); and PYNYLSTDV (SEQ ID NO: 9); and
  (ii) a second peptide comprising a sequence consisting of a HLA-A*2402-restricted immunogenic epitope,
  wherein said second peptide is an immunogenic epitope, which has an amino acid sequence selected from the group consisting of KYGVLLKTL (SEQ ID NO: 11); RYMRQFVAL (SEQ ID NO: 12); RYVSRLLGI (SEQ ID NO: 13); RYGKGWDLL (SEQ ID NO: 14); RYLVQVQAL (SEQ ID NO: 15); and RYWELSNHL (SEQ ID NO: 16) and is derived from the first peptide by substituting its N-terminal residue with an arginine or a lysine, and/or by substituting its C-terminal residue with a leucine, an isoleucine, or a phenylalanine.

4. A kit of parts comprising, in separate containers:
  (i) a first peptide comprising one or more HLA-A*2402-restricted cryptic epitopes that has an amino acid sequence selected from the group consisting of PYGVLLKTH (SEQ ID NO: 1); PYMRQFVAH (SEQ ID NO: 2); PYVSRLLGI (SEQ ID NO: 3); PYGKGWDLM (SEQ ID NO: 4); TYLVQVQAL (SEQ ID NO: 5); PYWELSNHE (SEQ ID NO: 6); PYDGIPARE (SEQ ID NO: 7); RYEFLWGPR (SEQ ID NO: 8) and PYNYLSTDV (SEQ ID NO: 9); and
  (ii) a second peptide comprising one or more HLA-A*2402-restricted immunogenic epitopes derived from the HLA-A*2402-restricted cryptic epitopes,
  wherein said second peptide is a chimeric polypeptide according to claim 2, and wherein the at least one immunogenic epitope comprised in the second peptide is cognate to at least one HLA-A*2402-restricted cyptic epitope comprised in the first peptide.

* * * * *